United States Patent
Liu et al.

(10) Patent No.: US 9,540,304 B2
(45) Date of Patent: *Jan. 10, 2017

(54) PROCESSES FOR PRODUCING AN ACETIC ACID PRODUCT HAVING LOW BUTYL ACETATE CONTENT

(71) Applicant: Celanese International Corporation, Irving, TX (US)

(72) Inventors: Yaw-Hwa Liu, Missouri City, TX (US); Mark O. Scates, Houston, TX (US)

(73) Assignee: CELANESE INTERNATIONAL CORPORATION, Irving, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/874,250

(22) Filed: Oct. 2, 2015

(65) Prior Publication Data

US 2016/0137576 A1 May 19, 2016

Related U.S. Application Data

(63) Continuation-in-part of application No. 14/694,932, filed on Apr. 23, 2015, now Pat. No. 9,260,369.

(60) Provisional application No. 62/079,991, filed on Nov. 14, 2014.

(51) Int. Cl.
*C07C 51/12* (2006.01)
*C07C 51/44* (2006.01)

(52) U.S. Cl.
CPC ............... *C07C 51/12* (2013.01); *C07C 51/44* (2013.01)

(58) Field of Classification Search
CPC .................................................... C07C 51/12
See application file for complete search history.

(56) References Cited

U.S. PATENT DOCUMENTS

| | | | |
|---|---|---|---|
| 4,609,504 A | 9/1986 | Gauthier-Lafaye et al. | |
| 4,733,006 A | 3/1988 | Singleton et al. | |
| 4,792,620 A | 12/1988 | Paulik et al. | |
| 5,625,095 A * | 4/1997 | Miura ..................... | C07C 51/12 562/519 |
| 5,756,836 A | 5/1998 | Shimizu et al. | |
| 6,303,813 B1 * | 10/2001 | Scates ..................... | C07C 51/12 562/517 |
| 6,573,403 B1 | 6/2003 | Joensen | |
| 6,657,078 B2 * | 12/2003 | Scates ..................... | C07C 51/12 562/519 |
| 7,683,212 B2 | 3/2010 | Kojima et al. | |
| 7,855,306 B2 | 12/2010 | Zinobile et al. | |
| 8,940,932 B2 | 1/2015 | Shimizu | |
| 8,957,248 B2 | 2/2015 | Miura et al. | |
| 9,073,843 B2 | 7/2015 | Shimizu et al. | |
| 9,115,071 B2 | 8/2015 | Shimizu et al. | |
| 9,260,369 B1 | 2/2016 | Liu et al. | |
| 2013/0264186 A1 | 10/2013 | Shimizu et al. | |
| 2013/0281735 A1 | 10/2013 | Shimizu et al. | |

FOREIGN PATENT DOCUMENTS

| | | |
|---|---|---|
| EP | 0 487 284 A2 | 5/1992 |
| JP | H04-266843 A | 9/1992 |
| JP | 3244350 | 1/2002 |
| JP | 3244351 | 1/2002 |
| WO | 2008/153708 A2 | 12/2008 |
| WO | 2013/137236 | 9/2013 |
| WO | 2014/115826 | 7/2014 |

OTHER PUBLICATIONS

Haynes, A. (2006, e-pub. May 25, 2006). "Acetic Acid Synthesis by Catalytic Carbonylation of Methanol," in Topics in Organometallic Chemistry, Catalytic Carbonylation Reactions, Springer-Verlag, Berlin, Heidelberg, 18:179-205.
Non-Final Office Action mailed on Aug. 18, 2015 for U.S. Appl. No. 14/694,932, 14 pages.
Japanese Office Action mailed on Aug. 10, 2015 for JP Patent Application No. 2015-101746, with English translation, 12 pages.
Japanese Office Action received in the corresponding Patent Application No. 2015-222664, dated Mar. 11, 2016.
International Search Report and Written Opinion mailed on Jan. 21, 2016 for International Application No. PCT/US2015/053843, 11 pages.

* cited by examiner

*Primary Examiner* — Paul A Zucker
(74) *Attorney, Agent, or Firm* — Kilpatrick Townsend & Stockton LLP

(57) ABSTRACT

A process for producing an acetic acid product having low butyl acetate content via a carbonylation reaction. The carbonylation reaction is carried out at a temperature from 100 to 300° C., a hydrogen partial pressure from 0.3 to 2 atm, and a rhodium catalyst concentration from 100 to 3000 wppm, based on the weight of the reaction medium. The butyl acetate concentration in the acetic acid product may be controlled by removing acetaldehyde from a stream derived from the reaction medium and/or by adjusting at least one of reaction temperature, hydrogen partial pressure, and metal catalyst concentration.

17 Claims, 5 Drawing Sheets

PROCESSES FOR PRODUCING AN ACETIC ACID PRODUCT HAVING LOW BUTYL ACETATE CONTENT

CROSS-REFERENCES TO RELATED APPLICATIONS

This patent application is a continuation-in-part of U.S. patent application Ser. No. 14/694,932, entitled "Processes For Producing An Acetic Acid Product Having Low Butyl Acetate Content," filed on Apr. 23, 2015, and claims priority from U.S. Provisional Patent Application No. 62/079,991, entitled "Processes For Producing An Acetic Acid Product Having Low Butyl Acetate Content," filed on Nov. 14, 2014, now U.S. Pat. No. 9,260,369 the disclosure of which is incorporated herein by reference in its entirety.

FIELD OF THE INVENTION

This invention relates to processes for producing acetic acid and, in particular, to processes for producing an acetic acid product having low butyl acetate content.

BACKGROUND OF THE INVENTION

Among currently employed processes for synthesizing acetic acid, one of the most useful, commercially, is the catalyzed carbonylation of methanol with carbon monoxide as taught in U.S. Pat. No. 3,769,329, herein incorporated by reference in its entirety. The carbonylation catalyst contains a metal catalyst, such as rhodium, which is either dissolved or otherwise dispersed in a liquid reaction medium or supported on an inert solid, along with a halogen-containing catalyst promoter, e.g., methyl iodide. The rhodium can be introduced into the reaction system in many forms. Likewise, because the nature of the halide promoter is not generally critical, a large number of suitable promoters, most of which are organic iodides, may be used. Most typically and usefully, the reaction is conducted by continuously bubbling carbon monoxide gas through a liquid reaction medium in which the catalyst is dissolved.

During the carbonylation of methanol, by-products are formed. One by-product is acetaldehyde. Reduction of acetaldehyde has been described in the art. For example, U.S. Pat. No. 5,756,836 teaches a process for producing a highly purified acetic acid characterized in that the process comprises the step of continuously reacting methanol and/or an aqueous solution of methyl acetate with carbon monoxide in a reactor. A treatment is conducted to limit the concentration of unsaturated compounds in crude acetic acid obtained in the process to 5 wppm or lower, and the resultant crude acetic acid is ozonized. The '836 patent also teaches a process for producing a highly purified acetic acid, characterized by the step of continuously reacting methanol and/or an aqueous solution of methyl acetate with carbon monoxide in a reactor while maintaining the concentration of acetaldehyde in a reaction fluid in the reactor at 1500 wppm or lower. The acetaldehyde concentration is controlled by conducting said reaction at a water content not greater than 10 wt. % and an acetaldehyde concentration of not greater than 1500 wppm to produce a crude acetic acid product mixture; sending the crude acetic acid product mixture to a distillation column to produce a high-boiling point fraction and a low-boiling point fraction; treating the low-boiling point fraction to reduce the content of acetaldehyde therein; and returning the treated low-boiling point fraction to the reaction system.

U.S. Pat. No. 5,625,095 also suggests that acetaldehyde concentration should be reduced. The '095 patent discloses a high purity acetic acid prepared by reacting methanol with carbon monoxide in the presence of a rhodium catalyst, iodide salts, and methyl iodide, wherein an acetaldehyde concentration in the reaction liquid is maintained at 400 wppm or lower. This may be attained by contacting the liquid containing carbonyl impurities with water to separate and remove the carbonyl impurities. After that, the liquid can be returned to the reactor.

U.S. Pat. No. 6,573,403 teaches a process for producing acetic acid which comprises charging reactants methanol, dimethyl ether, methyl acetate or any mixture thereof into a reactor containing: (1) a rhodium carbonylation catalyst, (2) an alkyl iodide or alkyl bromide, and (3) a hydrogenation catalyst, and contacting the reactants with carbon monoxide and hydrogen to produce acetic acid. The '403 patent further teaches that the addition of ruthenium compounds to the carbonylation reaction solution effectively reduces the formation of undesired carbonyl impurities whilst increasing the formation of ethanol, ethyl acetate and ethyl iodide, which are precursors for the formation of valuable propanoic acid.

Additional methods for removing permanganate reducing compounds (PRC's), such as acetaldehyde, are disclosed in U.S. Pat. Nos. 7,855,306 and 7,683,212. The '306 patent teaches a process for reducing and/or removing permanganate-reducing compounds or their precursors from intermediate streams during the formation of acetic acid. In particular, a low boiling overhead vapor stream from a light ends column is subjected to a single distillation to obtain an overhead that is subjected to an extraction to selectively remove and/or reduce PRC's from the process. The '212 patent teaches a method to produce acetic acid by continuously reacting methanol with carbon monoxide in the presence of a rhodium catalyst, an iodide salt, methyl iodide, methyl acetate, and water; and thereby producing acetic acid at a production rate of 11 mol/L·hr or more while keeping the acetaldehyde content of a reaction mixture to 500 wppm or less. The reaction is carried out at a carbon monoxide partial pressure in a gaseous phase of a reactor of 1.05 MPa or more and/or at a methyl acetate content of the reaction mixture of 2 percent by weight or more, to thereby keep the production rate of acetaldehyde to $\frac{1}{1500}$ or less that of acetic acid. The '212 patent teaches that this method can reduce production of by-products without reducing the reaction rate of acetic acid even at a low water content and a low hydrogen partial pressure in a reaction system.

U.S. Pat. No. 6,303,813 discloses methanol carbonylation methods which substantially reduce the production of carbonyl impurities, particularly acetaldehyde, crotonaldehyde, and 2-ethyl crotonaldehyde, by maintaining a partial pressure of hydrogen between about 0.4 and 4 psia at reaction total pressure of from about 15 to about 40 atmospheres total reaction pressure.

Although the above-described publications focus on suppressing or removing carbonyl impurities, such as acetaldehyde and crotonaldehyde from carbonylation reaction systems, little art exists concerning butyl acetate, which can be formed from these impurities. The need therefore exists for improved processes for producing a high-purity acetic acid product comprising low amounts of butyl acetate.

SUMMARY OF THE INVENTION

In one embodiment, there is provided a process for producing an acetic acid product comprising the steps of continuously carbonylating at least one member selected from the group consisting of methanol, dimethyl ether, and methyl acetate with carbon monoxide in a reactor in the presence of water, a rhodium catalyst, methyl iodide and lithium iodide to form a reaction medium. The carbonylation is carried out at a temperature from 150 to 250° C., a hydrogen partial pressure from 0.3 to 2 atm, e.g., from 0.3 to 1.5 atm and more preferably from 0.4 to 1.5 atm, and a rhodium catalyst concentration from 100 to 3000 wppm, e.g., from 400 to 1500 wppm, based on the weight of the reaction medium. The process further comprises removing acetaldehyde from a stream derived from the reaction medium to form the acetic acid product, and maintaining a butyl acetate concentration in the acetic acid product of less than or equal to 10 wppm. In one embodiment, the methanol may be introduced into the reactor in a methanol source comprising ethanol in an amount from 1 to 150 wppm ethanol. In one embodiment, the reaction medium comprises less than or equal to 1500 wppm acetaldehyde. The reaction medium may also comprise water in an amount from 0.1 to 4.1 wt. %. The reaction medium comprises methyl acetate in an amount from 0.5 to 30 wt. %, a rhodium catalyst in an amount from 200 to 3000 wppm, lithium iodide in an amount from 1 to 25 wt. %, and methyl iodide in an amount from 1 to 25 wt. %. In one embodiment, the acetic acid product comprises less than or equal to 250 wppm propionic acid, a displaced metal selected from the group consisting of silver, mercury, palladium and rhodium, a corrosion metal selected from the group consisting of nickel, iron, chromium, and molybdenum, and/or lithium. The displaced metal and/or corrosion in the acetic acid product may be in an amount of less than or equal to 500 wppb, and/or the acetic acid product may comprise less than or equal to 50 wppb lithium. In one embodiment, process for removing acetaldehyde from a stream derived from the reaction medium may comprise (a) separating at least a portion of the reaction medium to provide a vapor overhead stream comprising acetic acid and a liquid recycle; (b) distilling the vapor overhead stream to yield a side stream comprising acetic acid and a first overhead stream comprising methyl iodide, water, acetic acid, methyl acetate, and acetaldehyde; (c) distilling at least a portion of the first overhead stream to form a second overhead stream and a liquid phase residuum, wherein the second overhead stream is enriched with acetaldehyde with respect to the at least a portion of the first overhead stream; and (d) extracting the second overhead stream with water to obtain an aqueous acetaldehyde stream comprising acetaldehyde and a raffinate comprising methyl iodide. In one embodiment, the process further comprises condensing and biphasically separating the first overhead stream to form a light liquid phase and a heavy liquid phase, wherein the at least a portion of the first overhead stream distilled in step (c) comprises a portion of the light liquid phase and/or heavy liquid phase.

In another embodiment, there is provided a process for producing an acetic acid product comprising the steps of continuously carbonylating at least one member selected from the group consisting of methanol, dimethyl ether, and methyl acetate with carbon monoxide in a reactor in the presence of water, a rhodium catalyst, methyl iodide and lithium iodide to form a reaction medium. The carbonylating is carried out at a temperature from 150 to 250° C. and a hydrogen partial pressure from 0.3 to 2 atm, based on the weight of the reaction medium. The process further comprises removing acetaldehyde from a stream derived from the reaction medium to form the acetic acid product, contacting the acetic acid product with a metal-exchanged ion exchange resin, and maintaining a butyl acetate concentration in the acetic acid product of less than or equal to 10 wppm and maintaining an iodide concentration in the less than or equal to 100 wppb. In one embodiment, the methanol may be introduced into the reactor in a methanol source comprising ethanol in an amount from 1 to 150 wppm ethanol. In one embodiment, the reaction medium comprises less than or equal to 1500 wppm acetaldehyde. The reaction medium may also comprise water in an amount from 0.1 to 4.1 wt. %. The reaction medium comprises methyl acetate in an amount from 0.5 to 30 wt. %, a rhodium catalyst in an amount from 200 to 3000 wppm, lithium iodide in an amount from 1 to 25 wt. %, and methyl iodide in an amount from 1 to 25 wt. %. In one embodiment, the acetic acid product comprises less than or equal to 250 wppm propionic acid, a displaced metal selected from the group consisting of silver, mercury, palladium and rhodium, a corrosion metal selected from the group consisting of nickel, iron, chromium, and molybdenum, and/or lithium. The displaced metal and/or corrosion metal may be present in the acetic acid product in an amount of less than or equal to 500 wppb, and/or the acetic acid product may comprise less than or equal to 50 wppb lithium. In one embodiment, process for removing acetaldehyde from a stream derived from the reaction medium may comprise (a) separating at least a portion of the reaction medium to provide a vapor overhead stream comprising acetic acid and a liquid recycle; (b) distilling the vapor overhead stream to yield a side stream comprising acetic acid and a first overhead stream comprising methyl iodide, water, acetic acid, methyl acetate, and acetaldehyde; (c) distilling at least a portion of the first overhead stream to form a second overhead stream and a liquid phase residuum, wherein the second overhead stream is enriched with acetaldehyde with respect to the at least a portion of the first overhead stream; and (d) extracting the second overhead stream with water to obtain an aqueous acetaldehyde stream comprising acetaldehyde and a raffinate comprising methyl iodide. In one embodiment, the process further comprises condensing and biphasically separating the first overhead stream to form a light liquid phase and a heavy liquid phase, wherein the at least a portion of the first overhead stream distilled in step (c) comprises a portion of the light liquid phase and/or heavy liquid phase.

In another embodiment, there is provided a process for producing an acetic acid product, comprising providing a reaction medium comprising acetic acid, methanol, methyl acetate, less than or equal to 4.1 wt. % water, a rhodium catalyst, methyl iodide and lithium acetate; removing acetaldehyde from a stream derived from the reaction medium to form the acetic acid product; and maintaining a butyl acetate concentration in the acetic acid product of less than or equal to 10 wppm. In one embodiment, the methanol may be introduced into the reactor in a methanol source comprising ethanol in an amount from 1 to 150 wppm ethanol. In one embodiment, the reaction medium comprises less than or equal to 1500 wppm acetaldehyde. The reaction medium may also comprise water in an amount from 0.1 to 4.1 wt. %. The reaction medium comprises methyl acetate in an amount from 0.5 to 30 wt. %, a rhodium catalyst in an amount from 200 to 3000 wppm, lithium iodide in an amount from 1 to 25 wt. %, and methyl iodide in an amount from 1 to 25 wt. %. In one embodiment, the acetic acid product comprises less than or equal to 250 wppm propionic acid, a displaced metal selected from the group consisting of silver, mercury, palladium and rhodium, a corrosion metal selected from the group consisting of nickel, iron, chromium, and molybdenum, and/or lithium. The displaced metal and/or corrosion metal in the acetic acid product may be in an amount of less than or equal to 500 wppb, and/or the acetic acid product may comprise less than or equal to 50 wppb lithium. In one embodiment, process for removing acetaldehyde from a stream derived from the reaction medium may comprise (a) separating at least a portion of the reaction medium to provide a vapor overhead stream comprising acetic acid and a liquid recycle; (b) distilling the vapor overhead stream to yield a side stream comprising acetic acid and a first overhead stream comprising methyl iodide, water, acetic acid, methyl acetate, and acetaldehyde; (c) distilling at least a portion of the first overhead stream to form a second overhead stream and a liquid phase residuum, wherein the second overhead stream is enriched with acetaldehyde with respect to the at least a portion of the first overhead stream; and (d) extracting the second overhead stream with water to obtain an aqueous acetaldehyde stream comprising acetaldehyde and a raffinate comprising methyl iodide. In one embodiment, the process further comprises condensing and biphasically separating the first overhead stream to form a light liquid phase and a heavy liquid phase, wherein the at least a portion of the first overhead stream distilled in step (c) comprises a portion of the light liquid phase and/or heavy liquid phase.

In a further embodiment, there is provided a process for producing an acetic acid product, comprising the steps of continuously reacting methanol with carbon monoxide in the presence of a rhodium catalyst, lithium iodide, and methyl iodide to form a reaction medium, wherein the reaction is carried out at a temperature from 100 to 300° C. and a hydrogen partial pressure from 0.3 to 2 atm, wherein the reaction medium comprises rhodium in an a concentration from 100 to 3000 wppm. The process further comprises separating the acetic acid product from the reaction medium; determining the butyl acetate concentration in the acetic acid product; adjusting at least one of the temperature, the hydrogen partial pressure and the rhodium catalyst concentration when the butyl acetate concentration in the acetic acid product is greater than 10 wppm; and removing acetaldehyde from a stream derived from the reaction medium to maintain an acetaldehyde concentration of less than or equal to 1500 wppm in the reaction medium.

BRIEF DESCRIPTION OF THE DRAWINGS

The present invention will be better understood in view of the appended non-limiting figures, wherein.

DETAILED DESCRIPTION OF THE INVENTION

Figure 1:
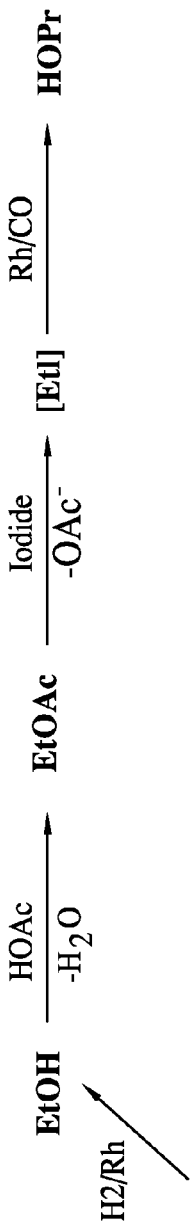
FIG. 1 shows a schematic of acetic acid reaction by-products and impurities derived from acetaldehyde.
Figure 1:
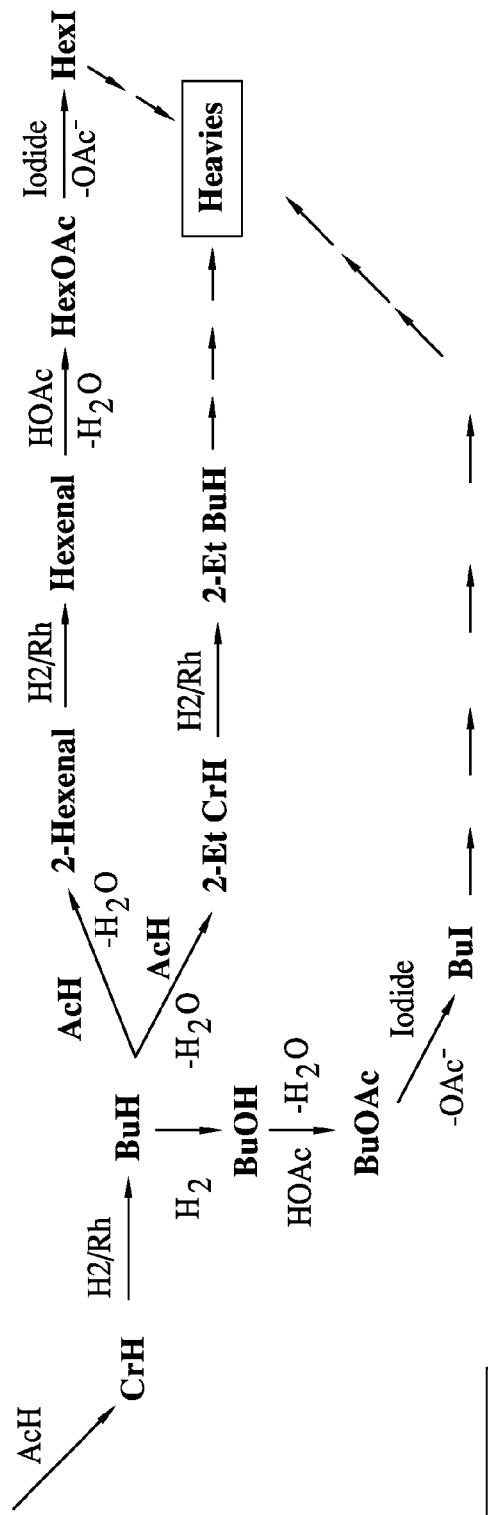

At the outset, it should be noted that in the development of any such actual embodiment, numerous implementation—specific decisions must be made to achieve the developer's specific goals, such as compliance with system related and business related constraints, which will vary from one implementation to another. In addition, the processes disclosed herein can also comprise components other than those cited or specifically referred to, as is apparent to one having average or reasonable skill in the art.

In the summary and this detailed description, each numerical value should be read once as modified by the term "about" (unless already expressly so modified), and then read again as not so modified unless otherwise indicated in context. Also, in the summary and this detailed description, it should be understood that a concentration range listed or described as being useful, suitable, or the like, is intended that any and every concentration within the range, including the end points, is to be considered as having been stated. For example, a range "from 1 to 10" is to be read as indicating each and every possible number along the continuum between about 1 and about 10. Thus, even if specific data points within the range, or even no data points within the range, are explicitly identified or refer to only a few specific data points, it is to be understood that inventors appreciate and understand that any and all data points within the range are to be considered to have been specified, and that inventors possessed knowledge of the entire range and all points within the range.

Throughout the entire specification, including the claims, the following terms have the indicated meanings unless otherwise specified.

As used in the specification and claims, "near" is inclusive of "at." The term "and/or" refers to both the inclusive "and" case and the exclusive "or" case, and is used herein for brevity. For example, a mixture comprising acetic acid and/or methyl acetate may comprise acetic acid alone, methyl acetate alone, or both acetic acid and methyl acetate.

All percentages are expressed as weight percent (wt. %), based on the total weight of the particular stream or composition present, unless otherwise noted. Room temperature is 25° C. and atmospheric pressure is 101.325 kPa unless otherwise noted.

For purposes herein: acetic acid may be abbreviated as "AcOH";
acetaldehyde may be abbreviated as "AcH";
methyl acetate may be abbreviated "MeAc";
methanol may be abbreviated "MeOH";
methyl iodide may be abbreviated as "MeI";
hydrogen iodide may be abbreviated as "HI";
carbon monoxide may be abbreviated "CO"; and
dimethyl ether may be abbreviated "DME".

HI refers to either molecular hydrogen iodide or dissociated hydriodic acid when at least partially ionized in a polar medium, typically a medium comprising at least some water. Unless otherwise specified, the two are referred to interchangeably. Unless otherwise specified, HI concentration is determined via acid-base titration using a potentiometric end point. In particular, HI concentration is determined via titration with a standard lithium acetate solution to a potentiometric end point. It is to be understood that for purposes herein, the concentration of HI is not determined by subtracting a concentration of iodide assumed to be associated with a measurement of corrosion metals or other non H+ cations from the total ionic iodide present in a sample.

It is to be understood that HI concentration does not refer to iodide ion concentration. HI concentration specifically refers to HI concentration as determined via potentiometric titration.

This subtraction method is an unreliable and imprecise method to determine relatively lower HI concentrations (i.e., less than about 5 weight percent) due to the fact that it assumes all non-H+ cations (such as cations of Fe, Ni, Cr, Mo) are associated with iodide anion exclusively. In reality, a significant portion of the metal cations in this process can be associated with acetate anion. Additionally, many of these metal cations have multiple valence states, which adds even more unreliability to the assumption on the amount of iodide anion which could be associated with these metals. Ultimately, this method gives rise to an unreliable determination of the actual HI concentration, especially in view of the ability to perform a simple titration directly representative of the HI concentration.

For purposes herein, an "overhead" or "distillate" of a distillation column refers to at least one of the lower boiling condensable fractions which exits at or near the top, (e.g., proximate to the top), of the distillation column, and/or the condensed form of that stream or composition. Obviously, all fractions are ultimately condensable, yet for purposes herein, a condensable fraction is condensable under the conditions present in the process as readily understood by one of skill in the art. Examples of noncondensable fractions may include nitrogen, hydrogen, and the like. Likewise, an overhead stream may be taken just below the upper most exit of a distillation column, for example, wherein the lowest boiling fraction is a non-condensable stream or represents a de-minimis stream, as would be readily understood by one of reasonable skill in the art.

The "bottoms" or "residuum" of a distillation column refers to one or more of the highest boiling fractions which exit at or near the bottom of the distillation column, also referred to herein as flowing from the bottom sump of the column. It is to be understood that a residuum may be taken from just above the very bottom exit of a distillation column, for example, wherein the very bottom fraction produced by the column is a salt, an unusable tar, a solid waste product, or a de-minimis stream as would be readily understood by one of reasonable skill in the art.

For purposes herein, distillation columns comprise a distillation zone and a bottom sump zone. The distillation zone includes everything above the bottom sump zone, i.e., between the bottom sump zone and the top of the column. For purposes herein, the bottom sump zone refers to the lower portion of the distillation column in which a liquid reservoir of the higher boiling components is present (e.g., the bottom of a distillation column) from which the bottom or residuum stream flows upon exiting the column. The bottom sump zone may include reboilers, control equipment, and the like.

It is to be understood that the term "passages", "flow paths", "flow conduits", and the like in relation to internal components of a distillation column are used interchangeably to refer to holes, tubes, channels, slits, drains, and the like, which are disposed through and/or which provide a path for liquid and/or vapor to move from one side of the internal component to the other side of the internal component. Examples of passages disposed through a structure such as a liquid distributor of a distillation column include drain holes, drain tubes, drain slits, and the like, which allow a liquid to flow through the structure from one side to another.

Average residence time is defined as the sum total of all liquid volume hold-up for a given phase within a distillation zone divided by the average flow rate of that phase through the distillation zone. The hold-up volume for a given phase can include liquid volume contained in the various internal components of the column including collectors, distributors and the like, as well as liquid contained on trays, within downcomers, and/or within structured or random packed bed sections.

Acetic Acid Product

The present invention relates to processes for producing acetic acid product, comprising carbonylating at least one member selected from the group consisting of methanol, dimethyl ether and methyl acetate in the presence of water, a metal catalyst such as rhodium, methyl iodide and a halide salt, preferably lithium iodide, to form a reaction medium. The carbonylating step is carried out at a temperature from 150 to 250° C., a hydrogen partial pressure from 0.3 to 2 atm, and a metal catalyst, e.g., rhodium, at a concentration from 100 to 3000 wppm, based on the weight of the reaction medium, while maintaining a butyl acetate concentration in the acetic acid product of less than or equal to 10 wppm, e.g., less than or equal to 9 wppm, less than or equal to 8 wppm, less than or equal to 6 wppm, or less than or equal to 2 wppm.

Due to the difficulty in removing butyl acetate from acetic acid in a carbonylation purification process, butyl acetate concentration in the acetic acid product is not easily controlled, especially if low amounts of butyl acetate are desired. Butyl acetate has a higher boiling point than acetic acid, which makes distillation separation of butyl acetate not readily available. Butyl acetate is not a permanganate-reducing compounds, which may be removed using an acetaldehyde removal system. Instead, butyl acetate is an impurity, which, when present in concentrations above 10 wppm, can lead to degradation of acetic acid product quality. An acetic acid product having butyl acetate concentration at 10 wppm or less may be referred to herein as a high-purity acetic acid product. In one embodiment, the butyl acetate concentration in the purity acetic acid product is at least partially controlled by removing acetaldehyde from a stream derived from the reaction medium. The butyl acetate concentration in the acetic acid product may also be maintained by adjusting at least one parameter selected from the group consisting of the reaction temperature, the hydrogen partial pressure, the metal catalyst concentration, and the water concentration. It has been surprisingly and unexpectedly discovered that by removing acetaldehyde from a stream derived from the reaction medium and by controlling at least one parameter selected from the group consisting of reaction temperature, hydrogen partial pressure, and metal catalyst concentration in the reaction medium, the amount of butyl acetate in the acetic acid product can be advantageously controlled at 10 wppm or less. As a consequence of these controls, the amount of other impurities in the acetic acid product, such as propionic acid, may also be controlled at less than or equal to 250 wppm, e.g., less than or equal to 225 wppm, less than or equal to 200 wppm, less than or equal to 175 wppm, less than or equal to 150 wppm, or less than or equal to 100 wppm.

In addition to the carbonylation reaction, several side reactions occur in the reaction medium. Without being bound by theory, FIG. 1 shows various by-products and impurities that may be formed in a carbonylation process by hydrogenation and aldol condensation reactions. When acetaldehyde is present in the reaction medium, the acetaldehyde is converted to crotonaldehyde via an aldol condensation reaction. Crotonaldehyde may then be hydrogenated to butyl aldehyde, which may then be hydrogenated to butanol. Finally, butanol may react with acetic acid to form butyl acetate. In addition to butyl aldehyde being hydrogenated to butanol, butyl aldehyde may react with acetaldehyde to form additional impurities, as shown in FIG. 1. FIG. 1 also indicates that acetaldehyde concentration is only one factor affecting the butyl acetate concentration in the final acetic acid product. Thus, acetaldehyde concentration in the reaction medium is not an accurate predictor, by itself, of the final butyl acetate content, and other parameters may be adjusted to achieve the desired butyl acetate content in the acetic acid product.

Carbonylation Reaction Step

Figure 2:
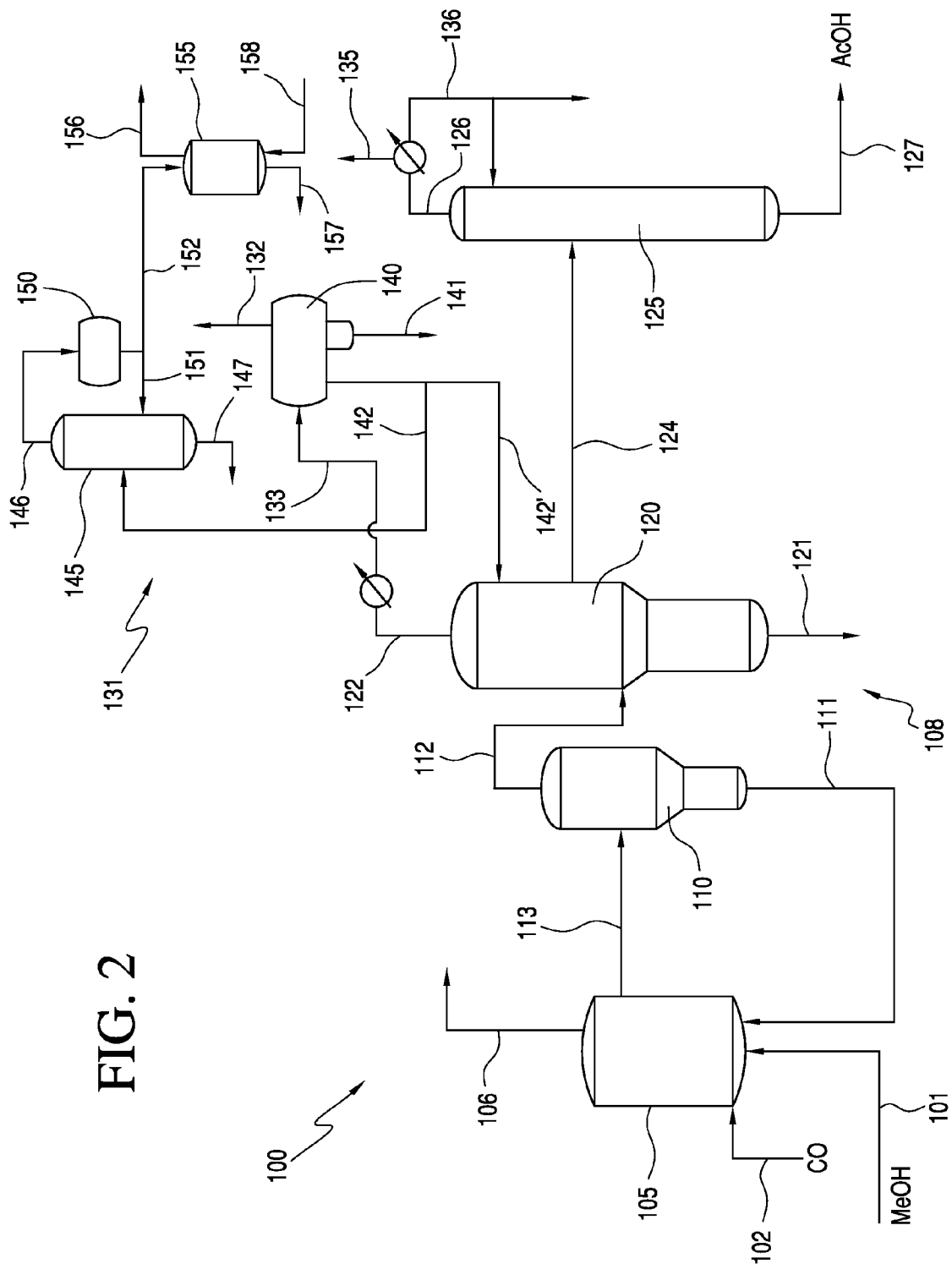
FIG. 2 shows a schematic of an acetic acid production process in accordance with the present invention.

Exemplary reaction and acetic acid recovery system 100 is shown in FIG. 2. As shown, methanol-containing feed stream 101 and carbon monoxide-containing feed stream 102 are directed to liquid phase carbonylation reactor 105, in which the carbonylation reaction occurs.

Methanol-containing feed stream 101 may comprise at least one member selected from the group consisting of methanol, dimethyl ether, and methyl acetate. Methanol-containing feed stream 101 may be derived in part from a fresh feed or may be recycled from the system. At least some of the methanol and/or reactive derivative thereof may be converted to, and hence be present as, methyl acetate in the liquid medium by esterification with acetic acid.

Typical reaction temperatures for carbonylation will be from 150 to 250° C., with the temperature range of 180 to 225° C. being a preferred range. The carbon monoxide partial pressure in the reactor can vary widely but is typically from 2 to 30 atm, e.g., from 3 to 10 atm. The hydrogen partial pressure in the reactor is typically from 0.3 to 2 atm, e.g., from 0.3 to 1.5 atm, or from 0.4 to 1.5 atm. In embodiments, the hydrogen partial pressure in the reactor may be greater than or equal to 0.3 atm, e.g., greater than or equal to 0.4 atm, greater than or equal to 0.45 atm, greater than or equal to 0.5 atm, greater than or equal to 0.6 atm, or greater than or equal to 0.7 atm. It is understood at 1 atm is equivalent to approximately 101.33 kPa and 14.70 psi. As hydrogen partial pressure is increased, the water-gas shift reaction of carbon monoxide and water to carbon dioxide and hydrogen is affected since the carbon dioxide component is decreased. Increasing the hydrogen partial pressure also allows for a reduction in temperature and therefore a reduction in operating costs. Finally, increasing the hydrogen partial pressure improves metal catalyst activity, e.g., rhodium activity, by shifting the reaction equilibria to more rhodium in the active form. However, as hydrogen partial pressure is increased, impurity production is also increased. Typically, low hydrogen partial pressure of less than 0.3 atm may be desirable to control impurities, including by not limited to acetaldehyde, butyl acetate, and/or propionic acid. Advantageously, the present invention can achieve both the stabilization of the rhodium catalyst with hydrogen partial pressure of greater than 0.3 atm and the avoidance of the large amounts of impurities, such as butyl acetate, and/or propionic acid, in the acetic acid product. This advantage is achieved by removing acetaldehyde from a stream derived from the reaction medium when recovering the acetic acid product.

Because of the partial pressure of by-products and the vapor pressure of the contained liquids, the total reactor pressure will range from 15 to 40 atm. The production rate of acetic acid may be from 5 to 50 mol/L·h, e.g., from 10 to 40 mol/L·h, and preferably from 15 to 35 mol/L·h.

Carbonylation reactor 105 is preferably either a mechanically-stirred vessel, a vessel with an educted or pump-around mixing, or a bubble-column type vessel. The reactor can be with or without an agitator, within which the reacting liquid or slurry contents are maintained, preferably automatically, a predetermined level, which preferably remains substantially constant during normal operation. Into carbonylation reactor 105, fresh methanol, carbon monoxide, and sufficient water are continuously introduced as needed to maintain suitable concentrations in the reaction medium.

The metal catalyst may comprise a Group VIII metal. Suitable Group VIII catalysts include rhodium and/or iridium catalysts. A rhodium catalyst may be added in any suitable form, according to teachings well known in the art, such that the catalyst solution comprising rhodium is present as an equilibrium mixture including $[Rh(CO)_2I_2]$-anion. Iodide salts may be optionally maintained in the reaction mixtures of the processes described herein in the form of a soluble salt of an alkali metal or alkaline earth metal, quaternary ammonium, phosphonium salt or mixtures thereof. In certain embodiments, the catalyst co-promoter is lithium iodide, lithium acetate, or mixtures thereof. The catalyst co-promoter may be added as a non-iodide salt that will generate an iodide salt. The catalyst co-promoter may be introduced directly into the reaction system. Alternatively, the iodide salt may be generated in-situ since under the operating conditions of the reaction system, a wide range of non-iodide salt precursors will react with methyl iodide or hydroiodic acid in the reaction medium to generate the corresponding catalyst co-promoter. Additional detail regarding rhodium catalysis and iodide salt generation may be found in U.S. Pat. Nos. 5,001,259; 5,026,908; 5,144,068 and 7,005,541, which are incorporated herein by reference in their entirety. The carbonylation of methanol utilizing iridium catalyst is well known and is generally described in U.S. Pat. Nos. 5,942,460; 5,932,764; 5,883,295; 5,877,348; 5,877,347; and 5,696,284; which are also incorporated herein by reference in their entirety.

The halogen-containing catalyst promoter of the catalyst system consists of a halogen compound comprising an organic halide, such as, alkyl, aryl, and substituted alkyl or aryl halides. Preferably, the halogen-containing catalyst promoter is present in the form of an alkyl halide. Even more preferably, the halogen-containing catalyst promoter is present in the form of an alkyl halide in which the alkyl radical corresponds to the alkyl radical of the feed alcohol, which is being carbonylated. Thus, the halide, promoter used in the carbonylation of methanol to acetic acid, may include methyl halide, and more preferably, methyl iodide.

The components of the reaction medium are maintained within defined limits to ensure sufficient production of acetic acid. The reaction medium contains a concentration of the metal catalyst, e.g., rhodium catalyst, in an amount from 100 to 3000 wppm, e.g., from 200 to 3000 wppm, from 400 to 2000 wppm, or from 400 to 1500 wppm as rhodium. The concentration of water in the reaction medium is maintained to be less than or equal to 14 wt. %, e.g., from 0.1 wt. % to 14 wt. %, from 0.2 wt. % to 10 wt. % or from 0.25 wt. % to 5 wt. %. Preferably, the reaction is conducted under low water conditions and the reaction medium contains water in an amount that is less than or equal to 4.1 wt. %, e.g., less than or equal to 3.5 wt. %, less than 3 or equal to wt. %, or less than or equal to 2 wt. %. In terms of ranges, the reaction medium contains water in an amount from 0.1 to 4.1 wt. % water, e.g., from 0.1 to 3.5 wt. % water, from 0.1 to 3 wt. % or from 0.5 to 2.8 wt. %. The concentration of methyl iodide in the reaction medium is maintained to be from 1 to 25 wt. %, e.g., from 5 to 20 wt. %, from 4 to 13.9 wt. %. The concentration of iodide salt, e.g., lithium iodide, in the reaction medium is maintained to be from 1 to 25 wt. %, e.g., from 2 to 20 wt. %, from 3 to 20 wt. %. The concentration of methyl acetate in the reaction medium is maintained to be from 0.5 to 30 wt. %, e.g., from 0.3 to 20 wt. %, from 0.6 to 4.1 wt. %. The concentration of acetic acid in the reaction medium is generally more than 30 wt. %, e.g., more than 40 wt. % or more than 50 wt. %. The above amounts are based on the total weight of the reaction medium.

In one embodiment, there is provided a process for producing an acetic acid product comprising the steps of continuously carbonylating at least one member selected from the group consisting of methanol, dimethyl ether, and methyl acetate, with carbon monoxide in a reaction medium in a reactor. The reaction medium comprises methyl acetate in an amount from 0.5 to 30 wt. %, a rhodium catalyst in an amount from 200 to 3000 wppm, iodide salt, e.g., lithium iodide, in an amount from 1 to 25 wt. %, and methyl iodide in an amount from 1 to 25 wt. %. The carbonylating is carried out at a temperature from 150 to 250° C., and a hydrogen partial pressure from 0.3 to 2 atm. The process further comprises removing acetaldehyde from a stream derived from the reaction medium to form the acetic acid product, and maintaining a butyl acetate concentration in the acetic acid product of less than or equal to 10 wppm. In a further embodiment, the reaction medium may contain water in an amount that is less than or equal to 4.1 wt. %, based on the total weight of the reaction medium.

In embodiments, the lithium compound introduced into the reactor is selected from the group consisting of lithium acetate, lithium carboxylates, lithium carbonates, lithium hydroxide, other organic lithium salts, and mixtures thereof. In embodiments, the lithium compound is soluble in the reaction medium. In an embodiment, lithium acetate dihydrate is used as the source of the lithium compound.

Lithium acetate reacts with hydrogen iodide according to the following equilibrium reaction (I) to form lithium iodide and acetic acid:

LiOAc+HI⇌LiI+HOAc   (I)

Lithium acetate is thought to provide improved control of hydrogen iodide concentration relative to other acetates, such as methyl acetate, present in the reaction medium. Without being bound by theory, lithium acetate is a conjugate base of acetic acid and thus reactive toward hydrogen iodide via an acid-base reaction. This property is thought to result in an equilibrium of the reaction (I) which favors reaction products over and above that produced by the corresponding equilibrium of methyl acetate and hydrogen iodide. This improved equilibrium is favored by water concentrations of less than or equal to 4.1 wt. % in the reaction medium. In addition, the relatively low volatility of lithium acetate compared to methyl acetate allows the lithium acetate to remain in the reaction medium except for volatility losses and small amounts of entrainment into the vapor crude product. In contrast, the relatively high volatility of methyl acetate allows the material to distill into the purification train, rendering it more difficult to control methyl acetate. Lithium acetate is much easier to maintain and control in the process when the concentrations of hydrogen iodide are consistently low. Accordingly, a relatively small amount of lithium acetate may be employed relative to the amount of methyl acetate needed to control hydrogen iodide concentrations in the reaction medium. It has further been discovered that lithium acetate is at least three times more effective than methyl acetate in promoting the addition of methyl iodide oxidative to the rhodium [I] complex.

In embodiments, the concentration of lithium acetate in the reaction medium is maintained at greater than or equal to 0.3 wt. %, greater than or equal to 0.35 wt. %, greater than or equal to 0.4 wt. %, greater than or equal to 0.45 wt. %, or greater than or equal to 0.5 wt. %, and/or in embodiments, the concentration of lithium acetate in the reaction medium is maintained at less than or equal to 0.7 wt. %, less than or equal to 0.65 wt. %, less than or equal to 0.6 wt. %, or less than or equal to 0.55 wt. %.

It has been discovered that an excess of lithium acetate in the reaction medium can adversely affect the other compounds in the reaction medium, resulting in a decrease in productivity. Conversely, it has been discovered that a lithium acetate concentration in the reaction medium below about 0.3 wt. % is unable to maintain the desired hydrogen iodide concentrations in the reaction medium of below 1.3 wt. %.

In embodiments, the lithium compound may be introduced continuously or intermittently into the reaction medium. In embodiments, the lithium compound is introduced during reactor start up. In embodiments, the lithium compound is introduced intermittently to replace entrainment losses.

In some embodiments, the desired reaction rates are obtained even at low water concentrations by maintaining in the reaction medium an ester of the desired carboxylic acid and an alcohol, desirably the alcohol used in the carbonylation, and an additional iodide ion that is over and above the iodide ion that is present as hydrogen iodide. A desired ester is methyl acetate. The additional iodide ion is desirably an iodide salt, with lithium iodide (LiI) being preferred. It has been found, as described in U.S. Pat. No. 5,001,259, that when low water concentrations, methyl acetate and lithium iodide act as rate promoters only when relatively high concentrations of each of these components are present, and that the promotion is higher when both of these components are present simultaneously.

The carbonylation reaction of methanol to acetic acid product may be carried out by contacting the methanol feed with gaseous carbon monoxide bubbled through an acetic acid solvent reaction medium containing the rhodium catalyst, methyl iodide promoter, methyl acetate, and additional soluble iodide salt, at conditions of temperature and pressure suitable to form the carbonylation product. It is generally recognized that it is the concentration of iodide ion in the catalyst system, not the cation associated with the iodide, that is important and not the cation associated with the iodide. It is also recognized that at a given molar concentration of iodide, the nature of the cation is not as significant as the effect of the iodide concentration. Any metal iodide salt, or any iodide salt of any organic cation, or other cations such as those based on amine or phosphine compounds (optionally quaternary cations), can be used in the reaction medium, provided that the salt is sufficiently soluble in the reaction medium to provide the desired level of the iodide. When the iodide is a metal salt, preferably it is an iodide salt of a member of the group consisting of the metals of Group IA and Group IIA of the periodic table, as set forth in the "Handbook of Chemistry and Physics" published by CRC Press, Cleveland, Ohio, 2002-03 (83rd edition). In particular, alkali metal iodides are useful, with lithium iodide being particularly suitable. In the low-water carbonylation process, the additional iodide ion over and above the iodide ion present as hydrogen iodide is generally present in the catalyst solution in amounts such that the total iodide ion concentration is from 1 to 25 wt. %, the methyl acetate concentration is from 0.5 to 30 wt. %, and the methyl iodide concentration is from 1 to 25 wt. %. The rhodium catalyst is generally present in amounts from 200 to 3000 wppm.

The reaction medium may also contain impurities that should be controlled to avoid byproduct formation. One impurity in the reaction medium may be ethyl iodide, which is carbonylated to propionic acid. Applicant has further discovered that the formation of ethyl iodide may be affected by numerous variables, including the concentration of acetaldehyde, ethyl acetate, methyl acetate and methyl iodide in the reaction medium. Additionally, ethanol content in the methanol source, hydrogen partial pressure and hydrogen content in the carbon monoxide source have been discovered to affect ethyl iodide concentration in the reaction medium and, consequently, propionic acid concentration in the acetic acid product.

In embodiments, the propionic acid concentration in the acetic acid product may further be maintained at below 250 wppm. This can be achieved by maintaining the ethyl iodide concentration in the reaction medium at less than or equal to 750 wppm without removing propionic acid from the acetic acid product.

In embodiments, the ethyl iodide concentration in the reaction medium and propionic acid in the acetic acid product may be present in a weight ratio from 3:1 to 1:2. In embodiments, the acetaldehyde:ethyl iodide concentration in the reaction medium is maintained at a weight ratio from 2:1 to 20:1.

In embodiments, the ethyl iodide concentration in the reaction medium may be maintained by controlling at least one of the hydrogen partial pressure, the methyl acetate concentration, the methyl iodide concentration, and/or the acetaldehyde concentration in the reaction medium.

In embodiments, the concentration of ethyl iodide in the reaction medium is maintained/controlled to be less than or equal to 750 wppm, or e.g., less than or equal to 650 wppm, or less than or equal to 550 wppm, or less than or equal to 450 wppm, or less than or equal to 350 wppm. In embodiments, the concentration of ethyl iodide in the reaction medium is maintained/controlled at greater than or equal to 1 wppm, or e.g., greater than or equal to 5 wppm, or greater than or equal to 10 wppm, or greater than or equal to 20 wppm, or greater than or equal to 25 wppm, and less than or equal to 650 wppm, or e.g., less than or equal to 550 wppm, or less than or equal to 450 wppm, or less than or equal to 350 wppm.

In embodiments, the weight ratio of ethyl iodide in the reaction medium to propionic acid in the acetic acid product may range from 3:1 to 1:2, or e.g., from 5:2 to 1:2, or from 2:1 to 1:2, or from 3:2 to 1:2.

In embodiments, the weight ratio of acetaldehyde to ethyl iodide in the reaction medium may range from 20:1 to 2:1, or e.g., from 15:1 to 2:1 or from 9:1 to 2:1.

In a typical carbonylation process, carbon monoxide is continuously introduced into the carbonylation reactor, desirably below the agitator. The agitator may be used to stir the contents. The gaseous feed preferably is thoroughly dispersed through the reacting liquid by this stirring means. Gaseous purge stream 106 desirably is vented from the reactor 105 to prevent buildup of gaseous by-products and to maintain a set carbon monoxide partial pressure at a given total reactor pressure. In one embodiment, the gaseous purge stream 106 contains low amounts of hydrogen iodide, e.g., less than or equal to 1 wt. %, less than or equal to 0.9 wt. %, less than or equal to 0.8 wt. %, less than or equal to 0.7 wt. %, or less than or equal to 0.5 wt. %. Hydrogen iodide in excess of these amounts may increase the duty on the scrubber to prevent hydrogen iodide from being purged. The temperature of the reactor may be controlled and the carbon monoxide feed is introduced at a rate sufficient to maintain the desired total reactor pressure. Stream 106 comprising the liquid reaction medium exits reactor 105.

The acetic acid production system preferably includes separation system 108 employed to recover the acetic acid and recycle metal catalyst, methyl iodide, methyl acetate, and other system components within the process. One or more of the recycle streams may be combined prior to being introduced into the reactor. The separation system also preferably controls water and acetic acid content in the carbonylation reactor, as well as throughout the system, and facilitates permanganate reducing compound ("PRC") removal. PRC's may include acetaldehyde, acetone, methyl ethyl ketone, butylaldehyde, crotonaldehyde, 2-ethyl crotonaldehyde, 2-ethyl butyraldehyde, and the aldol condensation products thereof. In one embodiment, a suitable potassium permanganate test is JIS K1351 (2007).

Flash Vessel

The reaction medium is drawn off from the carbonylation reactor 105 at a rate sufficient to maintain a constant level therein and is provided to flash vessel 110 via stream 113. The flash separation may be carried out at a temperature from 80° C. to 200° C., under an absolute pressure from 1 to 10 atm. In flash vessel 110, the reaction medium is separated in a flash separation step to obtain a vapor product stream 112 comprising acetic acid and less volatile catalyst phase as a liquid recycle 111 comprising a catalyst-containing solution.

In addition to acetic acid, vapor product stream 112 also comprises methyl iodide, methyl acetate, water, PRC's. Dissolved gases exiting reactor 105 and entering flash vessel 110 comprise a portion of the carbon monoxide and may also contain gaseous by-products such as methane, hydrogen, and carbon dioxide. Such dissolved gases exit flash vessel 110 as part of the vapor product stream 112. In one embodiment, carbon monoxide in gaseous purge stream 106 is fed to the base of flash vessel 110 to enhance rhodium stability. The catalyst-containing solution in liquid recycle 111 may be predominantly acetic acid and may also contain the rhodium and the iodide salt along with lesser quantities of methyl acetate, methyl iodide, and water. The catalyst-containing solution in liquid recycle 111 is recycled to the reactor, as discussed above.

In one embodiment, vapor product stream 112 comprises acetic acid, methyl iodide, methyl acetate, water, acetaldehyde, and hydrogen iodide. In one embodiment, vapor product stream 112 comprises acetic acid in an amount from 45 to 75 wt. %, methyl iodide in an amount from 20 to 50 wt. %, methyl acetate in an amount of less than or equal to 9 wt. %, and water in an amount of less than or equal to 15 wt. %, based on the total weight of the vapor product stream. In another embodiment, vapor product stream 112 comprises acetic acid in an amount from 45 to 75 wt. %, methyl iodide in an amount from 24 to less than 36 wt. %, methyl acetate in an amount of less than or equal to 9 wt. %, and water in an amount of less than or equal to 15 wt. %, based on the total weight of the vapor product stream. More preferably, vapor product stream 112 comprises acetic acid in an amount from 55 to 75 wt. %, methyl iodide in an amount from 24 to 35 wt. %, methyl acetate in an amount from 0.5 to 8 wt. %, and water in an amount from 0.5 to 14 wt. %. In yet a further preferred embodiment, vapor product stream 112 comprises acetic acid in an amount from 60 to 70 wt. %, methyl iodide in an amount from 25 to 35 wt. %, methyl acetate in an amount from 0.5 to 6.5 wt. %, and water in an amount from 1 to 8 wt. %. The acetaldehyde concentration in the vapor product stream may be in an amount from 0.005 to 1 wt. %, based on the total weight of the vapor product stream, e.g., from 0.01 to 0.8 wt. %, or from 0.01 to 0.7 wt. %. In some embodiments the acetaldehyde may be present in amounts less than or equal to 0.01 wt. %. Vapor product stream 112 may comprise hydrogen iodide in an amount less than or equal to 1 wt. %, e.g., less than or equal to 0.5 wt. %, or less than or equal to 0.1 wt. %, based on the total weight of the vapor product stream. Vapor product stream 112 is preferably substantially free of, i.e., contains less than or equal to 0.0001 wt. %, propionic acid, based on the total weight of the vapor product stream.

Liquid recycle stream 111 comprises acetic acid, the metal catalyst, corrosion metals, as well as other various compounds. In one embodiment, liquid recycle stream comprises acetic acid in an amount from 60 to 90 wt. %; metal catalyst in an amount from 0.01 to 0.5 wt. %; corrosion metals (e.g., nickel, iron and chromium) in a total amount from 10 to 2500 wppm; lithium iodide in an amount from 5 to 20 wt. %; methyl iodide in an amount from 0.5 to 5 wt. %; methyl acetate in an amount from 0.1 to 5 wt. %; water in an amount from 0.1 to 8 wt. %; acetaldehyde in an amount of less than or equal to 1 wt. % (e.g., from 0.0001 to 1 wt. % acetaldehyde); and hydrogen iodide in an amount of less than or equal to 0.5 wt. % (e.g., from 0.0001 to 0.5 wt. % hydrogen iodide).

Recovery of Acetic Acid

The distillation and recovery of acetic acid is not particularly limited for the purposes of the present invention. In contrast to previous methods that recover acetic acid from the vapor product stream, the present invention may recover acetic acid from both the vapor product stream, and/or a liquid stream that is condensed from a portion of the vapor product stream enriched in acetic acid.

As shown in FIG. 2, vapor product stream 112 is directed to a first column 120, also referred to as a light ends column. Distillation yields a low-boiling overhead vapor stream 122, a purified acetic acid product that preferably is removed via a side stream 124, and a high-boiling residue stream 121. In one embodiment, low-boiling overhead vapor stream 122 comprises water in an amount from 40 to 80 wt. %, methyl acetate, methyl iodide, and carbonyl impurities including acetaldehyde. Side stream 124 may comprise acetic acid in an amount from 85 to 98 wt. %, water in an amount from 1 to 5 wt. %, methyl iodide in an amount from 0.1 to 5 wt. %, and methyl acetate in an amount from 0.1 to 5 wt. %. Acetic acid, removed via side stream 124, preferably is subjected to further purification, such as in a second column 125, also referred to as a drying column. The side stream 124 is then separated to form overhead stream 126 that primarily comprises water, and bottoms stream 127 that primarily comprises acetic acid, e.g., the acetic acid product. Propionic acid in column 125 is concentrated with the acetic acid product in an amount of less than or equal to 250 wppm and is not removed from the acetic acid product. In some embodiments, the acetic acid product may be taken as a side stream (not shown) from column 125. This avoids the need for an additional separation step for removing propionic acid from acetic acid and provides many advantages, for example, dispensing the needs for heavy ends removal.

Overhead stream 126 may comprise water in an amount from 50 to 90 wt. %, e.g., from 50 to 75 wt. %. Methyl acetate and methyl iodide are also removed from the side stream and concentrated in the overhead stream. Drying column bottoms stream 127 preferably comprises acetic acid. In preferred embodiments, drying column bottoms stream 127 comprises acetic acid in an amount greater than or equal to 90 wt. %, e.g., greater than or equal to 95 wt. % or greater than or equal to 98 wt. % and comprises less than or equal to 250 wppm propionic acid. Drying column bottoms stream 127 may be further processed, e.g., by passing through an ion exchange resin, prior to being stored or transported for commercial use.

Low-boiling overhead vapor stream 122, separated from first column 120, contains a reaction component, such as methyl iodide, methyl acetate, and water. It is preferable to retain these reaction components within the process. Low-boiling overhead vapor stream 122 is condensed in a heat exchanger to form stream 133. At least a portion of stream 133 may be directed to a PRC's removal unit 131, discussed herein. Optionally, a portion of stream 133 which is recycled to reactor 105 and/or refluxed first column 120. Similarly, overhead stream 126 from second column 125 contains a reaction component, such as methyl iodide, methyl acetate, and water, and it is preferable to retain these reaction components within the process. Overhead stream 126 is condensed in a heat exchanger to form stream 136, which is recycled to reactor 105 and/or refluxed second column 125. An offgas component may be vented via line 135 from condensed low-boiling overhead vapor stream 126. Similar to the condensed low-boiling overhead vapor stream in stream 133, condensed overhead stream in stream 136 may also be separated to form an aqueous phase and an organic phase, and these phases may be recycled or refluxed as needed to maintain the concentrations in the reaction medium. In some embodiments, in addition to the condenser, there may be an overhead decanter for collecting the condensed overhead stream 136. The average residence time of the condensed low-boiling overhead vapor stream 136 in overhead decanter may be greater than or equal to 1 minute, e.g., greater than or equal to 3 minutes, greater than or equal to 5 minutes, or greater than or equal to 10 minutes, and/or the average residence time is less than or equal to 60 minutes, e.g., less than or equal to 45 minutes, less than or equal to 30 minutes, or less than or equal to 25 minutes. High amounts of ethyl iodide in the reaction medium in excess of 750 wppm, which is not removed and then may be carried through the purification process, may cause problems phasing in the decanter by forming a third layer or emulsion between the phases. Because ethyl iodide does not have a means to be removed directly in the process, it is important to prevent a buildup of ethyl iodide in the reaction medium. High amounts of ethyl iodide in the reaction medium can become concentrated to form an undesirable emulsion in the decanter. The emulsion causes poor separation which cannot easily be overcome by increasing the residence time. In some embodiments, the third layer or emulsion may also comprise alkanes. The alkanes, however, are controlled by controlling the acetaldehyde in the reaction medium.

Thus, in one embodiment, there is provided a process for producing an acetic acid product, comprising the steps of continuously carbonylating at least one member selected from the group consisting of methanol, dimethyl ether, and methyl acetate with carbon monoxide in a reactor in the presence of water, a metal catalyst, methyl iodide and a halide salt to form a reaction medium. The carbonylating is carried out while maintaining an ethyl iodide concentration in the reaction medium at less than or equal to 750 wppm. The process further comprises separating a reaction medium formed in a reactor in a flash vessel to form a liquid recycle and a vapor product stream, distilling the vapor product stream in a first column to obtain a side stream and a low boiling overhead vapor stream, condensing the low boiling overhead vapor stream and biphasically separating the condensed stream to form a heavy liquid phase and a light liquid phase in a decanter under conditions sufficient to prevent an emulsion between the heavy liquid phase and a light liquid phase, and recovering an acetic acid product from the side stream, wherein the acetic acid product comprises propionic acid in an amount of less than or equal to 250 wppm.

PRC Removal System (PRS)

The condensed overhead from the first column, either a portion of light liquid phase and/or heavy liquid phase, when condensed and phased, may be separated and directed to acetaldehyde or PRC removal system, to recover methyl iodide and methyl acetate, during the acetaldehyde removal process. Without being bound by theory, ethyl iodide tends to concentrate in the heavy liquid phase. Thus, when treating the heavy liquid phase with the PRC removal system, the ethyl iodide may be recycled back to the reactor. Each of the light liquid phase and/or heavy liquid phase contain PRC's in an amount of less than or equal to 1 wt. %, and the process may include removing carbonyl impurities, such as acetaldehyde.

As known in the art, PRC's deteriorate the quality of the acetic acid product and may be removed in suitable impurity removal columns and absorbers as described in U.S. Pat. Nos. 6,143,930; 6,339,171; 7,223,883; 7,223,886; 7,855,306; 7,884,237; 8,889,904; and US Pub. Nos. 2006/0011462, which are incorporated herein by reference in their entirety. Carbonyl impurities, such as acetaldehyde, may react with iodide catalyst promoters to form alkyl iodides, e.g., ethyl iodide, propyl iodide, butyl iodide, pentyl iodide, hexyl iodide, etc. Also, because many impurities originate with acetaldehyde, it is desirable to remove carbonyl impurities from at least one of the liquid light phase and/or heavy liquid phase. As described herein, when a PRC removal system is used, an alkane removal system is not used.

The portion of light liquid phase and/or heavy liquid phase fed to the acetaldehyde or PRC removal system may vary from 1% to 99% of the mass flow of either the light liquid phase 133 and/or heavy liquid phase 134, e.g., from 1 to 50%, from 2 to 45%, from 5 to 40%, 5 to 30% or 5 to 20%. Also in some embodiments, a portion of both the light liquid phase and heavy liquid phase may be fed to the acetaldehyde or PRC removal system. The portion of the light liquid phase not fed to the acetaldehyde or PRC removal system may be refluxed to the first column or recycled to the reactor, as described herein. The portion of the heavy liquid phase not fed to the acetaldehyde or PRC removal system may be recycled to the reactor. Although a portion of heavy liquid phase may be refluxed to the first column, it is more desirable to return the methyl iodide enriched heavy liquid phase to the reactor.

In one embodiment, a portion of light liquid phase and/or heavy liquid phase is fed to a distillation column which enriches the overhead thereof to have acetaldehyde and methyl iodide. Depending on the configuration, there may be two separate distillation columns, and the overhead of the second column may be enriched in acetaldehyde and methyl iodide. Dimethyl ether, which may be formed in-situ, may also be present in the overhead. The overhead may be subject to one or more extraction stages to remove a raffinate enriched in methyl iodide and an extractant. A portion of the raffinate may be returned to the distillation column, first column, overhead decanter and/or reactor. For example, when the heavy liquid phase is treated in the PRC removal system, it may be desirable to return a portion the raffinate to either the distillation column or reactor. Also, for example, when the light liquid phase is treated in the PRC removal system, it may be desirable to return a portion of the raffinate to either the first column, overhead decanter, or reactor. In some embodiments, the extractant may be further distilled to remove water, which is returned to the one or more extraction stages. The column bottoms, which contains more methyl acetate and methyl iodide than light liquid phase, may also be recycled to reactor and/or refluxed to first column.

The PRS may contain a single extraction step or multiple extraction stages, as described for example in U.S. Pat. No. 7,223,886. It optionally includes multistage countercurrent extraction. According to various embodiments, one or more streams derived from either or both (i) the PRS distillation column and/or (ii) the PRS extraction stage, for example, may be returned to the system, e.g., either or both (i) the light ends removal column and/or (ii) the drying column of the separation system for the acetic acid production system. For example, a first portion, e.g., an aliquot portion, of a bottoms stream from a PRS column may be directed to light ends column 120 for further processing. A second portion, e.g., an aliquot portion, of a bottoms stream from a PRS column may be directed to drying column 125, preferably the upper portion of drying column 125, for further processing. As another example, a raffinate from a PRS extraction unit, notably containing methyl iodide, may be returned to the system, e.g., light ends column or drying column; alternatively, the raffinate may be added directly to decanter 140 and/or may be returned to reactor 105.

For purposes of the present specification and claims, the overhead streams and overhead decanters of the light ends removal column and the drying column are considered to be part of the light ends removal column and/or the drying column.

As indicated above, either phase of the low-boiling overhead vapor stream 133 may be subsequently processed to remove PRC's.

For purposes of the present specification, it should be understood that the term "aliquot portion" refers to both: (i) a portion of a parent stream that has the same composition as the parent stream from which it is derived, and (ii) a stream comprising a portion of a parent stream that has the same composition as the parent stream from which it is derived and one or more additional streams that have been combined therewith. Thus, directing a return stream comprising an aliquot portion of a PRS distillation bottoms stream to the light ends column encompasses the direct transfer of a portion of the PRS distillation bottoms stream to the light ends column as well as the transfer of a derivative stream comprising (i) a portion of the PRS distillation bottoms stream and (ii) one or more additional streams that are combined therewith prior to introduction into the light ends column. An "aliquot portion" would not include, for example, streams formed in a distillation step or a phase separation step, which would not be compositionally the same as the parent stream from which they are derived nor derived from such a stream.

One of ordinary skill in the art having the benefit of this disclosure can design and operate a PRS distillation column to achieve the desired results. Accordingly, the practice of this process is not necessarily limited to specific characteristic of a particular distillation column or the operation characteristics thereof, such as the total number of stages, the feed point, reflux ratio, feed temperature, reflux temperature, column temperature profile, and the like.

In some cases, it may be advantageous to remove PRCs, primarily aldehydes such as acetaldehyde, from a low-boiling overhead vapor stream of a light ends distillation column, more preferably from the condensed light phase of a low-boiling overhead vapor stream 133 from light ends distillation column 120.

One or more of the streams from PRS 131 may be returned to the system, e.g., recycled, either directly or indirectly. The PRS preferably includes at least one distillation column and at least one extraction column to reduce and/or remove PRCs. US Patent Publication No. 2011/0288333, which is hereby incorporated by reference, describes various PRS embodiments that may be employed with the present process.

In one embodiment, as shown in FIG. 2, PRS 131 comprises a column 145, an accumulator 150, and an extractor 155. At least a portion of low-boiling overhead vapor stream 133 is directed to decanter 140 to form a heavy phase stream 141 and a light phase 142. Optionally, a portion of stream 142 is returned to column 120 via stream 142'. Additionally, a portion of heavy phase 141 may be returned to reactor 105. Optionally, a slip stream (not shown), e.g., from 5 to 40 vol. % or from 5 to 20 vol. %, of heavy phase 141 is directed to PRS 131. An offgas component may be vented via line 132 from decanter 140. In other embodiments (not shown), a larger portion of heavy phase 141 may be directed to PRS, e.g., from 40 to 100 vol. % heavy phase, from 60 to 100 vol. % or from 80 to 100 vol. %. In these embodiments, light phase 142 may be refluxed to column 120 or optionally, a slip stream of light phase 142 may be directed to the PRS, e.g., from 5 to 40 vol. % or from 5 to 20 vol. %.

At least a portion of light phase 142 is directed to column 145 to form a vapor overhead stream 146 and a bottom process stream 147 comprising water, methyl acetate, methanol, and mixtures thereof. Vapor overhead stream 146 is passed through a condenser and collected in accumulator 150. A portion of the condensed vapor overhead stream may be returned to column 145 via line 151. Another portion of the condensed vapor overhead stream is directed to extractor 155 via line 152 to form waste stream 156 comprising at least one PRC, e.g., acetaldehyde, and process stream 157 comprising methyl iodide. An aqueous stream may be provided to extractor 155 via line 158 at a location to obtain a countercurrent flow.

DME may be present in the PRS in amount sufficient to reduce the solubility of methyl iodide in the aqueous extracted phase. Reducing the amount of methyl iodide in the aqueous extracted phase reduces losses of methyl iodide into waste stream 156. In some embodiments, this may allow multiple extractions as described in U.S. Pat. Nos. 7,223,886, and 8,076,507, the entireties of which are herein incorporated by reference. The amount of DME may vary depending on the methyl iodide concentrations, and in some embodiments, the amount of DME may range from 3 to 9 wt. %, e.g., from 4 to 8 wt. %. DME may be present in the PRS, formed in the PRS by adding water to the PRS (generally by adding water to column 145) or added to the PRS (generally by adding DME upstream of extractor 155).

Thus, in one embodiment, there is provided process for producing an acetic acid product, comprising the steps of continuously carbonylating at least one member selected from the group consisting of methanol, dimethyl ether, and methyl acetate with carbon monoxide in a reactor, in the presence of water, a metal catalyst, methyl iodide and a halide salt to form a reaction medium, wherein the carbonylating is carried out while maintaining an ethyl iodide concentration in the reaction medium at less than or equal to 750 wppm. The process further comprises separating a reaction medium formed in a reactor in a flash vessel to form a liquid recycle and a vapor product stream, distilling the vapor product stream in a first column to obtain a side stream and a low boiling overhead vapor stream, condensing the low boiling overhead vapor stream and biphasically separating the condensed stream to form a heavy liquid phase and a light liquid phase, separating a portion of the heavy liquid phase to remove acetaldehyde or other PRC's, and recovering an acetic acid product from the side stream, wherein the acetic acid product comprises propionic acid in an amount of less than or equal to 250 wppm.

Second Column

Acetic acid removed via side stream 123 preferably is subjected to further purification, such as in a second column 125 (also referred to as a drying column) and separates side stream 123 to form aqueous overhead stream 126, comprising primarily water, and product stream 127, comprising primarily acetic acid. Water from the side stream is concentrated in the aqueous overhead stream. The aqueous overhead comprises greater than or equal to 90% of the water in the side stream, e.g., greater than or equal to 95%, greater than or equal to 97%, greater than or equal to 99%. Aqueous overhead stream 126 may comprise water in an amount from 50 to 75 wt. %. In embodiments, aqueous overhead stream may comprise water in an amount of less than or equal to 75 wt. %, e.g., less than or equal to 70 wt. %, less than or equal to 65 wt. %. Methyl acetate and methyl iodide are also removed from the side stream and concentrated in the overhead stream. Product stream 127, preferably comprising or consisting essentially of acetic acid, may be withdrawn in the bottom of second column 125 or a side stream near the bottom. When withdrawn as a side stream near the bottom, the side stream may be a liquid or a vapor stream. In preferred embodiments, product stream 127 comprises acetic acid in an amount greater than or equal to 90 wt. %, e.g., greater than or equal to 95 wt. % or greater than or equal to 98 wt. %. Product stream 127 may be further processed, e.g., by passing through an ion exchange resin, prior to being stored or transported for commercial use.

In embodiments, the acetic acid product withdrawn from the second column may also be essentially anhydrous, for example, containing less than or equal to 0.2 wt. % water, e.g., less than or equal to 0.15 wt. % water, less than or equal to 0.12 wt. % water, less than or equal to 0.1 wt. % water, or less than or equal to 0.05 wt. % water.

To recover residue liquids from the vent stream, in particular lines 106, 132, 135, and 122, these lines may be fed to a scrubber that operates with chilled methanol and/or acetic acid to remove methyl acetate and methyl iodide. A suitable scrubber is described in U.S. Pat. No. 8,318,977, herein incorporated by reference in its entirety.

The distillation columns of the present invention may be a conventional distillation column, e.g., a plate column, a packed column, and others. Plate columns may include a perforated plate column, bubble-cap column, Kittel tray column, uniflux tray, or a ripple tray column. The theoretical number of plates a plate column may have is not particularly limited, and depending on the species of the component to be separate, a plate column may include up to 80 plates, e.g., from 2 to 80, from 5 to 60, from 5 to 50, or more preferably from 7 to 35. The distillation column may include a combination of different distillation apparatuses. For example, a combination of bubble-cap column and perforated plate column may be used as well as a combination of perforated plate column and a packed column.

The distillation temperature and pressure in the distillation system can suitably be selected depending on the condition, e.g., the species of the objective carboxylic acid and the species of the distillation column; or the removal target selected from the lower boiling point impurity and the higher boiling point impurity, according to the composition of the feed stream. For example, in a case where the purification of acetic acid is carried out by the distillation column, the inner pressure of the distillation column (usually, the pressure of the column top) may be from 0.01 to 1 MPa, e.g., from 0.02 to 0.7 MPa, and more preferably from 0.05 to 0.5 MPa, in terms of gauge pressure. Moreover, the distillation temperature for the distillation column, namely the inner temperature of the column at the temperature of the column top, can be controlled by adjusting the inner pressure of the column, and, for example, may be from 20 to 200° C., e.g., from 50 to 180° C., and more preferably about from 100 to 160° C.

The material of each member or unit associated with the distillation system, including the columns, valves, condensers, receivers, pumps, reboilers, and internals, and various lines, each communicating to the distillation system may be made of suitable materials such as glass, metal, ceramic, or combinations thereof, and is not particularly limited to a specific one. According to the present invention, the material of the foregoing distillation system and various lines are a transition metal, or a transition-metal-based alloy, such as iron alloy, e.g., a stainless steel, nickel or nickel alloy, zirconium or zirconium alloy thereof, titanium or titanium alloy thereof, or aluminum alloy. Suitable iron-based alloys include those containing iron as a main component, e.g., a stainless steel that also comprises chromium, nickel, molybdenum and others. Suitable nickel-based alloys include those containing nickel as a main component and one or more of chromium, iron, cobalt, molybdenum, tungsten, manganese, and others, e.g., HASTELLOY™ and INCONEL™. Corrosion-resistant metals may be particularly suitable as materials for the distillation system and various lines.

Butyl Acetate Concentration in the Acetic Acid Product

As described herein, an acetic acid product, preferably a high purity acetic acid product, is formed by the processes of the present invention, preferably having a butyl acetate concentration of less than or equal to 10 wppm, e.g., less than or equal to 9 wppm, less than or equal to 8 wppm, less than or equal to 6 wppm, less than or equal to 2 wppm, or substantially free of butyl acetate, e.g., non-detectable. In terms of ranges, the acetic acid product may have a butyl acetate content from 0 to 10 wppm, e.g., from 0.1 to 9 wppm, from 0.2 to 8 wppm, from 0.3 to 6 wppm, or from 0.5 to 2 wppm.

One variable that may be adjusted to control the butyl acetate concentration of the acetic acid product is the acetaldehyde concentration in the reaction medium. As disclosed herein, butyl acetate is a by-product formed from acetic acid and butanol, which is derived ultimately from acetaldehyde as shown in FIG. 1. Thus, as acetaldehyde concentration is decreased, butyl acetate concentration is generally decreased. Acetaldehyde removal systems are described further herein, including in FIG. 2. Preferably, the acetaldehyde concentration in the reaction medium is maintained at less than or equal to 1500 wppm, e.g., less than or equal to 1200 wppm, less than or equal to 1000 wppm, less than or equal to 900 wppm, less than or equal to 750 wppm, less than or equal to 500 wppm, or less than or equal to 400 wppm. Thus, in one embodiment, there is provided a process for producing an acetic acid product comprising the steps of continuously carbonylating at least one member selected from the group consisting of methanol, dimethyl ether, and methyl acetate with carbon monoxide in a reactor, in the presence of water, a rhodium catalyst, methyl iodide and lithium iodide, to form a reaction medium. The carbonylating step is carried out at a temperature from 150 to 250° C. and a hydrogen partial pressure from 0.3 to 2 atm, and a metal catalyst concentration from 100 to 3000 wppm, based on the weight of the reaction medium. The process further comprises removing acetaldehyde from a stream derived from the reaction medium to form the acetic acid product, wherein the acetaldehyde concentration in the reaction medium is maintained at less than or equal to 1500 wppm; and maintaining a butyl acetate concentration in the acetic acid product of less than or equal to 10 wppm.

The acetaldehyde concentration in the reaction medium may be controlled by removing acetaldehyde from a stream derived from the reaction medium. This includes streams that are intended to be recycled to the reactor and derived from the vapor overhead stream, but excludes the acetic acid product stream. As described further herein a portion of overhead from the first column, also referred to as the light ends columns, may be treated to remove acetaldehyde.

In addition to removing acetaldehyde from a stream derived from the reaction medium, it has now been discovered that butyl acetate concentration in the acetic acid product may be controlled by adjusting at least one of reaction temperature, hydrogen partial pressure, and metal catalyst concentration in the reaction medium. The reaction temperature may be adjusted within the range of 150 to 250° C., e.g., within 180 to 225° C. Hydrogen partial pressure may be adjusted within the range of 0.3 to 2 atm, e.g., from 0.3 to 1.5 atm, from 0.4 to 1.5 atm, or from 0.3 to 1 atm. In some aspects, the hydrogen partial pressure greater than or equal to 0.3 atm, e.g., greater than or equal to 0.4 atm, greater than or equal to 0.45 atm, greater than or equal to 0.5 atm, greater than or equal to 0.6 atm, or greater than or equal to 0.7 atm. The hydrogen partial pressure may be adjusted by modifying the amount of hydrogen in the carbon monoxide source or by increasing reactor vent flows.

Based on the reaction mechanisms disclosed in FIG. 1, the concentration of propionic acid may be affected by the concentration butyl acetate in the acetic acid product. The concentration of propionic acid may be affected by other variables, including but not limited to, the concentration of acetaldehyde, ethanol content in the methanol source, hydrogen partial pressure, hydrogen content in the carbon monoxide source and reaction pressure. Ethanol may be present as an impurity in the methanol source, which may be present in an amount from 1 to 150 wppm, e.g., from 1 to 100 wppm, from 1 to 50 wppm or from 1 to 25 wppm. The ethanol concentration in the methanol source may vary. Optionally, the methanol source is purified to increase methanol content and reduce ethanol content prior to feeding to the carbonylation reactor. Therefore, the ethanol concentration in the methanol source may be less than 1 wppm, e.g., free of ethanol.

In one embodiment, a process is provided for producing an acetic acid product comprising the steps of continuously carbonylating a methanol source comprising ethanol in an amount from 1 to 150 wppm with carbon monoxide in a reactor in the presence of water, a rhodium catalyst, methyl iodide and lithium iodide to form a reaction medium, wherein the carbonylating is carried out at a temperature from 150 to 250° C., and a hydrogen partial pressure from 0.3 to 2 atm, removing acetaldehyde from a stream derived from the reaction medium to form the acetic acid product, and maintaining a butyl acetate concentration in the acetic acid product of less than or equal to 10 wppm.

The acetic acid product also preferably has a propionic acid concentration of less than or equal to 250 wppm, e.g., less than or equal to 225 wppm, less than or equal to 200 wppm, less than or equal to 175 wppm, less than or equal to 150 wppm, less than or equal to 100 wppm. In one embodiment, there is provided a process for producing an acetic acid product comprising the steps of continuously carbonylating at least one member selected from the group consisting of methanol, dimethyl ether, and methyl acetate with carbon monoxide in a reactor, in the presence of water, a rhodium catalyst, methyl iodide and lithium iodide, to form a reaction medium. The carbonylating step is carried out under these conditions: a temperature from 150 to 250° C., a hydrogen partial pressure from 0.3 to 2 atm, and a metal catalyst concentration from 100 to 3000 wppm, based on the weight of the reaction medium. The process further comprises removing acetaldehyde from a stream derived from the reaction medium to form the acetic acid product, maintaining a butyl acetate concentration in the acetic acid product of less than or equal to 10 wppm, and maintaining a propionic acid concentration of less than or equal to 250 wppm.

In addition to an acetic acid product having less than or equal to 10 wppm butyl acetate, it is also advantageous to produce a acetic acid product having low amounts of iodides, e.g., organic iodides including alkyl iodides. As is known, iodides in the acetic acid product are a harmful impurity to certain applications. For example, iodide impurities are particularly troublesome since they poison many of the catalysts employed in subsequent chemical conversions of the acetic acid. Iodides may be removed from the acetic acid product by contacting the acetic acid product with an ion exchange resin, such as a metal-exchanged ion exchange resin that comprises at least one metal selected from the group consisting of silver, mercury, palladium and rhodium. Suitable metal-exchanged ion exchange resins are described further herein. When an ion exchange resin is used, the acetic acid product, in one embodiment, may comprise iodides in an amount of less than or equal 100 weight parts per billion (wppb), e.g., less than or equal 90 wppb, less than or equal 50 wppb, less than or equal 25 wppb, less than or equal to 10 wppb, less than or equal to 10 wppb, less than or equal to 7 wppb, less than 5 or equal to wppb, less than or equal to 3 wppb, less than or equal to 2 wppb, or less than or equal to 1 wppb and/or, in embodiments, the acetic acid product may comprises iodides in an amount of greater than or equal to 1 wppb, e.g., greater than or equal to 5 wppb, greater than or equal to 10 wppb, or greater than or equal to 20 wppb.

In one embodiment, a process is provided for producing an acetic acid product comprising the steps of continuously carbonylating at least one member selected from the group consisting of methanol, dimethyl ether, and methyl acetate with carbon monoxide in a reactor, in the presence of water, a rhodium catalyst, methyl iodide and lithium iodide, to form a reaction medium. The carbonylating step is carried out at a temperature from 150 to 250° C. and under a hydrogen partial pressure from 0.3 to 2 atm, and a metal catalyst concentration from 100 to 3000 wppm, based on the weight of the reaction medium, removing acetaldehyde from a stream derived from the reaction medium to form the acetic acid product, contacting the acetic acid product with a metal-exchanged ion exchange resin, and maintaining a butyl acetate concentration in the acetic acid product of less than or equal to 10 wppm and maintaining an iodide concentration in the less than or equal to 100 wppb.

In some embodiments, when using a ion exchange resins, in particular a metal-exchanged ion exchange resins, some of the metals may become displaced and results in an undesirable buildup in the acetic acid product. For purposes of the present invention, the metal displaced are the metals used in the ion exchange resins, e.g., silver, mercury, palladium and rhodium. Thus, it is advantageous to operate the ion exchange resins in an manner that limits the displacement of these metals. The metals may be displaced by other metals in the system, such as corrosion metals, e.g., nickel, iron, chromium, and/or molybdenum, metals add to the purification train, e.g., potassium, or metals derived from/ generated by compounds in the reaction medium, e.g., such as lithium, phosphorus, or nitrogen. By limiting these metals from displacing the metals used in the ion exchange resins, iodides may be reduced/removed from an acetic acid product having less than or equal to 10 wppm butyl acetate, and the metal displaced from in the ion exchange resins, e.g., silver, mercury, palladium and rhodium, are also reduced/ removed. Thus, in one embodiment, the acetic acid product may comprise displaced metals, e.g., silver, mercury, palladium and rhodium, in a total amount of less than or equal to 500 wppb, e.g., less than or equal to 100 wppb, less than or equal to 90 wppb, less than or equal to 75 wppb, less than or equal to 50 wppb, or less than or equal to 25 wppb, and/or, in embodiments, the acetic acid product may comprises displaced metals in a total amount of greater than or equal to 1 wppb, e.g., greater than or equal to 5 wppb, greater than or equal to 10 wppb, or greater than or equal to 20 wppb.

In one embodiment, a process is provided for producing an acetic acid product comprising the steps of continuously carbonylating at least one member selected from the group consisting of methanol, dimethyl ether, and methyl acetate with carbon monoxide in a reactor, in the presence of water, a rhodium catalyst, methyl iodide and lithium iodide to form a reaction medium. The carbonylating is carried out at a temperature from 150 to 250° C., a hydrogen partial pressure from 0.3 to 2 atm, and a metal catalyst concentration from 100 to 3000 wppm, based on the weight of the reaction medium. The process further comprises removing acetaldehyde from a stream derived from the reaction medium to form the acetic acid product; contacting the acetic acid product with a metal-exchanged ion exchange resin; and maintaining a butyl acetate concentration in the acetic acid product of less than or equal to 10 wppm, maintaining an displaced metal in a total amount in the acetic acid product of less than or equal to 500 wppb, and optionally maintaining an iodide concentration in the acetic acid product of less than or equal to 100 wppb.

As indicated above, in one embodiment, to limit displaced metal concentration in the acetic acid product, it is preferable to limit the corrosion metals in the acetic acid product. Corrosion in the purification train is typically encountered regardless of the metallurgy of the columns and units associated with each column. For purposes of the present invention, corrosion metals include nickel, iron, chromium, and/or molybdenum. It may be advantageous to limit the corrosion metals in the acetic acid product because this produces a purified product and also reduces the amount of displaced metals as described above. In one embodiment, the acetic acid product may comprise corrosion metals, e.g., nickel, iron, chromium, and/or molybdenum, in a total amount of less than or equal to 1000 wppb, e.g., less than or equal to 750 wppb, less than or equal to 500 wppb, less than or equal to 250 wppb, less than or equal to 100 wppb, or less than or equal to 70 wppb, and/or, in embodiments, the acetic acid product may comprises corrosion metals in a total amount of greater than or equal to 1 wppb, e.g., greater than or equal to 5 wppb, greater than or equal to 10 wppb, greater than or equal to 25 wppb, or greater than or equal to 50 wppb.

In one embodiment, a process is provided for producing an acetic acid product comprising the steps of continuously carbonylating at least one member selected from the group consisting of methanol, dimethyl ether, and methyl acetate with carbon monoxide in a reactor, in the presence of water, a rhodium catalyst, methyl iodide and lithium iodide to form a reaction medium. The carbonylating is carried out under these conditions: a temperature from 150 to 250° C., a hydrogen partial pressure from 0.3 to 2 atm, and a metal catalyst concentration from 100 to 3000 wppm, based on the weight of the reaction medium. The process further comprises removing acetaldehyde from a stream derived from the reaction medium to form the acetic acid product, contacting the acetic acid product with a metal-exchanged ion exchange resin, and maintaining a butyl acetate concentration in the acetic acid product of less than or equal to 10 wppm, maintaining corrosion metals in a total amount of less than or equal to 1000 wppb, and optionally maintaining an iodide concentration in the less than or equal to 100 wppb.

Also indicated above, in one embodiment, to limit displaced metal concentration in the acetic acid product, it is preferable to limit the lithium in the acetic acid product. Lithium, in particular lithium cations, which may be derived from and/or generated by lithium compounds in the reaction medium, such as lithium iodide and/or lithium acetate. In one embodiment, prior to contacting the metal-exchanged ion exchange resin, the withdrawn crude acetic acid product may be contacted with a cation exchange resins to reduce and/or remove lithium. Suitable acid-form cation exchangers for removing metal ion contaminants in the present invention may comprise strong acid cation exchange resins, for example, strong acid macroreticular or macroporous resins, for example Amberlyst® 15 resin (DOW), Purolite C145, or Purolite CT145. The resin may also be an acid-form, strong acid cation exchange mesoporous resin. Chelating resins and zeolites may also be used. Removing lithium may provide two advantages: reducing the displaced metals in the acetic acid product and extending the lifetime of the metal-exchanged resin. In one embodiment, the acetic acid product comprises less than or equal to 50 wppb lithium, e.g., less than or equal to 25 wppb lithium, less than or equal to 10 wppb, or less than or equal to 5 wppb.

In one embodiment, a process is provided for producing an acetic acid product comprising the steps of continuously carbonylating at least one member selected from the group consisting of methanol, dimethyl ether, and methyl acetate with carbon monoxide in a reactor, in the presence of water, a rhodium catalyst, methyl iodide and lithium iodide to form a reaction medium. The carbonylating is carried out under these conditions: a temperature from 150 to 250° C., a hydrogen partial pressure from 0.3 to 2 atm, and a metal catalyst concentration from 100 to 3000 wppm, based on the weight of the reaction medium. The process further comprises removing acetaldehyde from a stream derived from the reaction medium to form the acetic acid product, contacting the acetic acid product with a metal-exchanged ion exchange resin, and maintaining a butyl acetate concentration in the acetic acid product of less than or equal to 10 wppm, maintaining less than or equal to 50 wppb lithium in the acetic acid product, and optionally maintaining an iodide concentration in the less than or equal to 100 wppb.

In one embodiment, it is desirable to limit amounts of iodides, displaced metals, corrosion metals, and/or lithium. In one embodiment, a process is provided for producing an acetic acid product comprising the steps of continuously carbonylating at least one member selected from the group consisting of methanol, dimethyl ether, and methyl acetate with carbon monoxide in a reactor, in the presence of water, a rhodium catalyst, methyl iodide and lithium iodide to form a reaction medium. The carbonylating is carried out under these conditions: a temperature from 150 to 250° C., a hydrogen partial pressure from 0.3 to 2 atm, and a metal catalyst concentration from 100 to 3000 wppm, based on the weight of the reaction medium. The process further comprises removing acetaldehyde from a stream derived from the reaction medium to form the acetic acid product, contacting the acetic acid product with a metal-exchanged ion exchange resin, and maintaining a butyl acetate concentration in the acetic acid product of less than or equal to 10 wppm, maintaining an displaced metal concentration of less than or equal to 500 wppb, maintaining an corrosion metal concentration of less than or equal to 1000 wppb, maintaining less than or equal to 50 wppb lithium in the acetic acid product, and optionally maintaining an iodide concentration in the less than or equal to 100 wppb.

Guard Bed

Carboxylic acid streams, e.g., acetic acid streams, that are contaminated with a halides and/or corrosion metals may be contacted with the ion exchange resin composition under a wide range of operating conditions. Preferably, the ion exchange resin composition is provided in a guard bed. The use of guard beds to purify contaminated carboxylic acid streams is well documented in the art, for example, U.S. Pat. Nos. 4,615,806; 5,653,853; 5,731,252; and 6,225,498, which are hereby incorporated by reference in their entirety. Generally, a contaminated liquid carboxylic acid stream is contacted with the ion exchange resin composition, which is preferably disposed in the guard bed. The halide contaminants, e.g., iodide contaminants, react with the metal to form metal iodides. In some embodiments, hydrocarbon moieties, e.g., methyl groups, that may be associated with the iodide may esterify the carboxylic acid. For example, in the case of acetic acid contaminated with methyl iodide, methyl acetate would be produced as a byproduct of the iodide removal. The formation of this esterification product typically does not have a deleterious effect on the treated carboxylic acid stream.

In one embodiment, the ion exchange resin is a metal-exchanged ion exchange resin and may comprise at least one metal selected from the group consisting of silver, mercury, palladium and rhodium. In one embodiment, at least 1% of the strong acid exchange sites of said metal-exchanged resin are occupied by silver. In another embodiment, at least 1% of the strong acid exchange sites of said metal-exchanged resin are occupied by mercury. The process may further comprise treating the purified acetic acid product with a cationic exchange resin to recover any silver, mercury, palladium or rhodium.

The pressure during the contacting step is limited only by the physical strength of the resin. In one embodiment, the contacting is conducted at pressures ranging from 0.1 MPa to 1 MPa, e.g., from 0.1 MPa to 0.8 MPa or from 0.1 MPa to 0.5 MPa. For convenience, however, both pressure and temperature preferably may be established so that the contaminated carboxylic acid stream is processed as a liquid. Thus, for example, when operating at atmospheric pressure, which is generally preferred based on economic considerations, the temperature may range from 17° C. (the freezing point of acetic acid) and 118° C. (the boiling point of acetic acid). It is within the purview of those skilled in the art to determine analogous ranges for product streams comprising other carboxylic acid compounds. The temperature of the contacting step preferably is kept relatively low to minimize resin degradation. In one embodiment, the contacting is conducted at a temperature ranging from 25° C. to 120° C., e.g., from 25° C. to 100° C. or from 50° C. to 100° C. Some cationic macroreticular resins typically begin degrading (via the mechanism of acid-catalyzed aromatic desulfonation) at temperatures of 150° C. Carboxylic acids having up to 5 carbon atoms, e.g., up to 3 carbon atoms, remain liquid at these temperatures. Thus, the temperature during the contacting should be maintained below the degradation temperature of the resin utilized. In some embodiments, the operating temperature is kept below temperature limit of the resin, consistent with liquid phase operation and the desired kinetics for halide removal.

The configuration of the guard bed within an acetic acid purification train may vary widely. For example, the guard bed may be configured after a drying column. Additionally or alternatively, the guard be may be configured after a heavy ends removal column or finishing column. Preferably the guard bed is configured in a position wherein the temperature acetic acid product stream is low, e.g., less than 120° C. or less than 100° C. Aside from the advantages discussed above, lower temperature operation provides for less corrosion as compared to higher temperature operation. Lower temperature operation provides for less formation of corrosion metal contaminants, which, as discussed above, may decrease overall resin life. Also, because lower operating temperatures result in less corrosion, vessels advantageously need not be made from expensive corrosion-resistant metals, and lower grade metals, e.g., standard stainless steel, may be used.

In one embodiment, the flow rate through the guard bed ranges from 0.1 bed volumes per hour ("BV/hr") to 50 BV/hr, e.g., 1 BV/hr to 20 BV/hr or from 6 BV/hr to 10 BV/hr. A bed volume of organic medium is a volume of the medium equal to the volume occupied by the resin bed. A flow rate of 1 BV/hr means that a quantity of organic liquid equal to the volume occupied by the resin bed passes through the resin bed in a one hour time period.

To avoid exhausting the resin with a purified acetic acid product that is high in total iodide concentration, in one embodiment the purified acetic acid product in bottoms stream 127 is contacted with a guard bed when total iodide concentration of the purified acetic acid product is less than 5 wppm, e.g., preferably less than 1 wppm. Total iodide concentration includes iodide from both organic, $C_1$ to $C_{14}$ alkyl iodides, and inorganic sources, such as hydrogen iodide. However, for purposes of the present invention ethyl iodide generally is not removed by guard beds. Instead methyl iodide and higher alkyl iodides, $C_6$ to $C_{14}$ alkyl iodides. A purified acetic acid composition is obtained as a result of the guard bed treatment. The purified acetic acid composition, in one embodiment, comprises less than or equal to 100 wppb iodides, e.g., less than or equal to 90 wppb, less than or equal to 50 wppb, or less than or equal to 25 wppb. In one embodiment, the purified acetic acid composition comprises less than or equal to 100 wppb corrosion metals, e.g., less than or equal to 750 wppb, less than or equal to 500 wppb, or less than or equal to 250 wppb. In terms of ranges, the purified acetic acid composition may comprise from 0 to 100 wppb iodides, e.g., from 1 to 50 wppb; and/or from 0 to 1000 wppb corrosion metals, e.g., from 1 to 500 wppb. In other embodiments, the guard bed removes at least 25 wt. % of the iodides from the crude acetic acid product, e.g., at least 50 wt. % or at least 75 wt. %. In one embodiment, the guard bed removes at least 25 wt. % of the corrosion metals from the crude acetic acid product, e.g., at least 50 wt. % or at least 75 wt. %.

As is evident from the figures and text presented above, a variety of embodiments are contemplated.

E1. A process for producing an acetic acid product comprising the steps of continuously carbonylating at least one member selected from the group consisting of methanol, dimethyl ether, and methyl acetate with carbon monoxide in a reactor in the presence of water, a rhodium catalyst, methyl iodide and lithium iodide to form a reaction medium, wherein the carbonylating is carried out at a temperature from 150 to 250° C., a hydrogen partial pressure from 0.3 to 2 atm, and a rhodium catalyst concentration from 100 to 3000 wppm, based on the weight of the reaction medium, removing acetaldehyde from a stream derived from the reaction medium to form the acetic acid product, and maintaining a butyl acetate concentration in the acetic acid product of less than or equal to 10 wppm.

E2. A process for producing an acetic acid product comprising the steps of continuously carbonylating at least one member selected from the group consisting of methanol, dimethyl ether, and methyl acetate with carbon monoxide in a reactor in the presence of water, a rhodium catalyst, methyl iodide and lithium iodide to form a reaction medium, wherein the carbonylating is carried out at a temperature from 150 to 250° C., and a hydrogen partial pressure from 0.3 to 2 atm, removing acetaldehyde from a stream derived from the reaction medium to form the acetic acid product, contacting the acetic acid product with a metal-exchanged ion exchange resin, and maintaining a butyl acetate concentration in the acetic acid product of less than or equal to 10 wppm and maintaining an iodide concentration in the acetic acid product of less than or equal to 100 wppb.

E3. The process of any one of embodiments E1 or E2, wherein the reaction medium comprises less than or equal to 1500 wppm acetaldehyde.

E4. The process of any one of embodiments E1-E3, wherein the reaction medium comprises water in an amount from 0.1 to 4.1 wt. %.

E5. The process of any one of embodiments E1-E4, wherein the rhodium catalyst concentration is from 400 to 1500 wppm.

E6. The process of any one of embodiments E1-E5, wherein the hydrogen partial pressure is from 0.3 to 1.5 atm.

E7. The process of any one of embodiments E1-E6, wherein the hydrogen partial pressure is from 0.4 to 1.5 atm.

E8. The process of any one of embodiments E1-E7, wherein the methanol is introduced into the reactor in a methanol source comprising ethanol in an amount from 1 to 150 wppm ethanol.

E9. The process of any one of embodiments E1-E8, wherein the acetic acid product comprises less than or equal to 250 wppm propionic acid.

E10. The process of any one of embodiments E1-E9, wherein the acetic acid product comprises a displaced metal selected from the group consisting of silver, mercury, palladium and rhodium, and the displaced metal in the acetic acid product in an amount of less than or equal to 500 wppb.

E11. The process of any one of embodiments E1-E10, wherein the acetic acid product comprises a corrosion metal selected from the group consisting of nickel, iron, chromium, and molybdenum, and the corrosion metal in the acetic acid product is in an amount of less than or equal to 1000 wppb.

E12. The process of any one of embodiments E1-E11, wherein the acetic acid product comprises less than or equal to 50 wppb lithium.

E13. The process of any one of embodiments E1-E12, wherein the reaction medium comprises methyl acetate in an amount from 0.5 to 30 wt. % methyl acetate, a rhodium catalyst in an amount from 200 to 3000 wppm, lithium iodide in an amount from 1 to 25 wt. %, and methyl iodide in an amount from 1 to 25 wt. %.

E14. The process of any one of embodiments E1-E13, wherein the removing acetaldehyde from a stream derived from the reaction medium comprises:
  (a) separating at least a portion of the reaction medium to provide a vapor overhead stream comprising acetic acid and a liquid recycle;
  (b) distilling the vapor overhead stream to yield a side stream comprising acetic acid and a first overhead stream comprising methyl iodide, water, acetic acid, methyl acetate, and acetaldehyde;
  (c) distilling at least a portion of the first overhead stream to form a second overhead stream and a liquid phase residuum, wherein the second overhead stream is enriched with acetaldehyde with respect to the at least a portion of the first overhead stream; and
  (d) extracting the second overhead stream with water to obtain an aqueous acetaldehyde stream comprising acetaldehyde and a raffinate comprising methyl iodide.

E15. The process of embodiment 14, further comprising condensing and biphasically separating the first overhead stream to form a light liquid phase and a heavy liquid phase, wherein the at least a portion of the first overhead stream distilled in step (c) comprises a portion of the light liquid phase.

E16. The process of embodiment 14, further comprising condensing and biphasically separating the first overhead stream to form a light liquid phase and a heavy liquid phase, wherein the at least a portion of the first overhead stream distilled in step (c) comprises a portion of the heavy liquid phase.

E17. A process for producing an acetic acid product, comprising:
  providing a reaction medium comprising acetic acid, methanol, methyl acetate, less than or equal to 4.1 wt. % water, a rhodium catalyst, methyl iodide and lithium acetate;
  removing acetaldehyde from a stream derived from the reaction medium to form the acetic acid product; and
  maintaining a butyl acetate concentration in the acetic acid product of less than or equal to 10 wppm.

E18. The process of embodiment E17, wherein the butyl acetate concentration is further maintained by adjusting at least one of reaction temperature, hydrogen partial pressure, and rhodium catalyst concentration in the reaction medium.

E19. The process of any one of embodiments E11 or E18, wherein the hydrogen partial pressure is from 0.3 to 2 atm.

E20. The process of any one of embodiments E11 or E18, wherein the hydrogen partial pressure is greater than or equal to 0.4 atm.

E21. The process of any one of embodiments E17-E20, further comprising contacting the acetic acid product with a metal-exchanged ion exchange resin E22. The process of any one of embodiments E17-E21, further comprising maintaining an iodide concentration in the acetic acid product of less than or equal to 100 wppb.

E23. The process of any one of embodiments E17-E22, wherein the acetic acid product comprises less than or equal to 250 wppm propionic acid.

E24. The process of any one of embodiments E17-E23, wherein the acetic acid product comprises a displaced metal selected from the group consisting of silver, mercury, palladium and rhodium, and the displaced metal in the acetic acid product is in an amount of less than or equal to 500 wppb.

E25. The process of any one of embodiments E17-E24, wherein the acetic acid product comprises a corrosion metal selected from the group consisting of nickel, iron, chromium, and molybdenum, and the corrosion metal in the acetic acid product is in an amount of less than or equal to 1000 wppb.

E26. The process of any one of embodiments E17-E25, wherein the acetic acid product comprises less than or equal to 50 wppb lithium.

E27. The process of any one of embodiments E17-E26, wherein the reaction medium comprises methyl acetate in an amount from 0.5 to 30 wt. %, a rhodium catalyst in an amount from 200 to 3000 wppm, lithium iodide in an amount from 1 to 25 wt. %, and methyl iodide in an amount from 1 to 25 wt. %.

E28. The process of any one of embodiments E17-E27, wherein the removing acetaldehyde comprises:
  (a) separating at least a portion of the reaction medium to provide a vapor overhead stream comprising acetic acid and a liquid recycle;
  (b) distilling the vapor overhead stream to yield a purified acetic acid product and a first overhead stream comprising methyl iodide, water, acetic acid, methyl acetate, and acetaldehyde;
  (c) distilling at least a portion of the first overhead stream to form a second overhead stream and a liquid phase residuum, wherein the second overhead stream is enriched with acetaldehyde with respect to the at least a portion of the first overhead stream; and
  (d) extracting the second overhead stream with water to obtain an aqueous acetaldehyde stream comprising acetaldehyde and a raffinate comprising methyl iodide.

E29. The process of embodiment E28, further comprising condensing and biphasically separating the first overhead stream to form a light liquid phase and a heavy liquid phase, wherein the at least a portion of the first overhead stream distilled in step (c) comprises the light liquid phase.

E30. The process of embodiment E28, further comprising condensing and biphasically separating the first overhead stream to form a light liquid phase and a heavy liquid phase, wherein the at least a portion of the first overhead stream distilled in step (c) comprises the heavy liquid phase.

E31. A process for producing an acetic acid product, comprising the steps of:
  continuously reacting methanol with carbon monoxide in the presence of a rhodium catalyst, lithium iodide, and methyl iodide to form a reaction medium, wherein the reaction is carried out at a temperature from 100 to 300° C. and a hydrogen partial pressure from 0.3 to 2 atm, wherein the reaction medium comprises rhodium in an a concentration from 100 to 3000 wppm,
  separating the acetic acid product from the reaction medium;
  determining the butyl acetate concentration in the acetic acid product;
  adjusting at least one of the temperature, the hydrogen partial pressure and the rhodium catalyst concentration when the butyl acetate concentration in the acetic acid product is greater than 10 wppm; and
  removing acetaldehyde from a stream derived from the reaction medium to maintain an acetaldehyde concentration of less than or equal to 1500 wppm in the reaction medium.

While the invention has been described in detail, modifications within the spirit and scope of the invention will be readily apparent to those of skill in the art. In view of the foregoing discussion, relevant knowledge in the art and references discussed above in connection with the Background and Detailed Description, the disclosures of which are all incorporated herein by reference. In addition, it should be understood that aspects of the invention and portions of various embodiments and various features recited below and/or in the appended claims may be combined or interchanged either in whole or in part. In the foregoing descriptions of the various embodiments, those embodiments which refer to another embodiment may be appropriately combined with other embodiments as will be appreciated by one of skill in the art. Furthermore, those of ordinary skill in the art will appreciate that the foregoing description is by way of example only, and is not intended to limit the invention.

EXAMPLES

The present invention will be better understood in view of the following non-limiting examples.

Example 1

Figure 3:
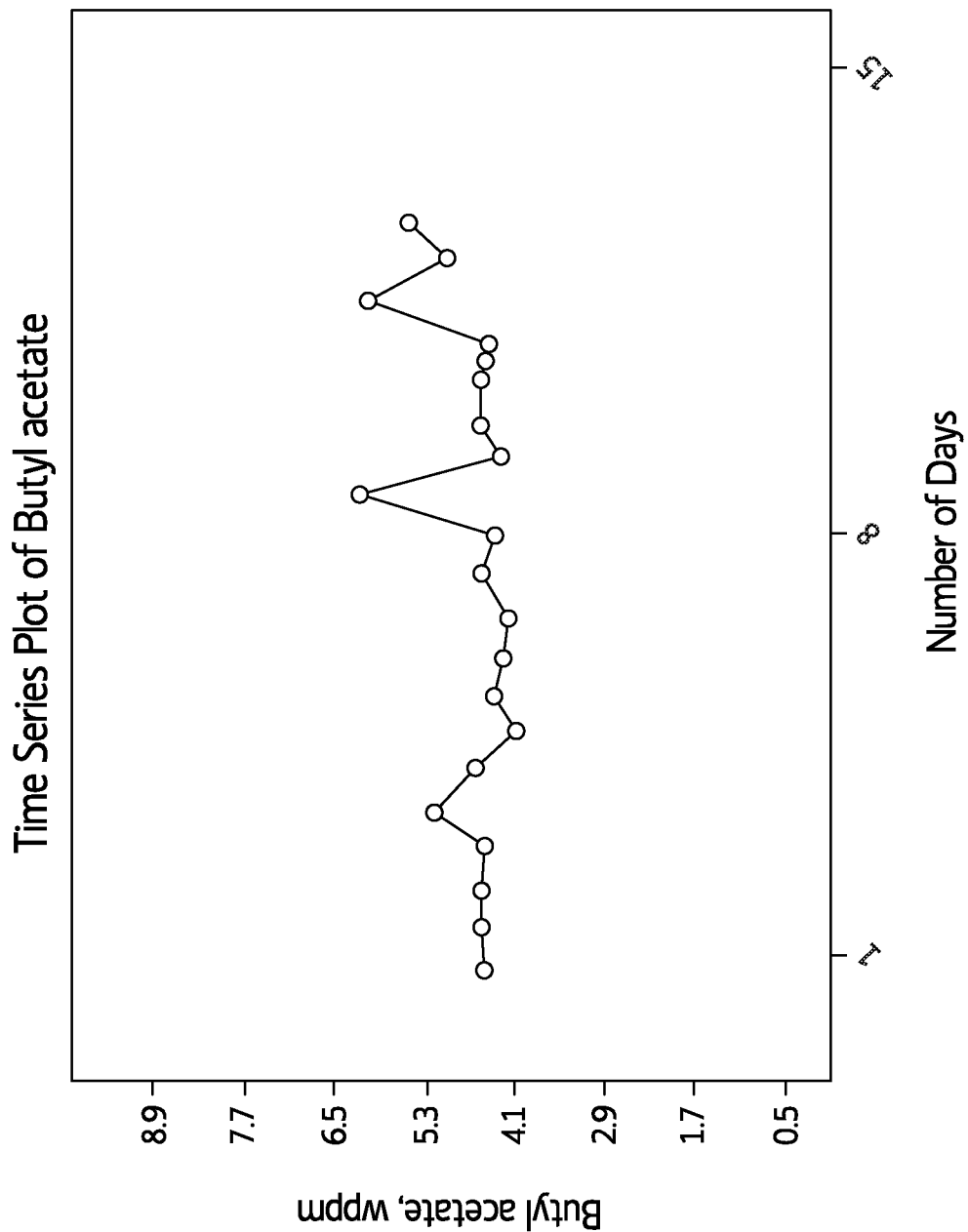
FIG. 3 shows a time series plot of butyl acetate in a final acetic acid product in accordance with the present invention.

An acetic acid product was prepared as follows. The reaction medium contained 10.8 wt. % methyl iodide, 2.5 wt. % methyl acetate, 4.1 wt. % water, 657 wppm rhodium and 8.4 wt. % lithium iodide. The reaction temperature was 191.8° C. The hydrogen partial pressure was 0.46 atm. The reaction medium was flashed and then separated in a light ends column, PRS, and drying column as described herein. The concentration of butyl acetate in the acetic acid product was measured over time. The results are shown in FIG. 3. Butyl acetate concentration was consistently below 8 wppm in the acetic acid product.

Example 2

Figure 4:
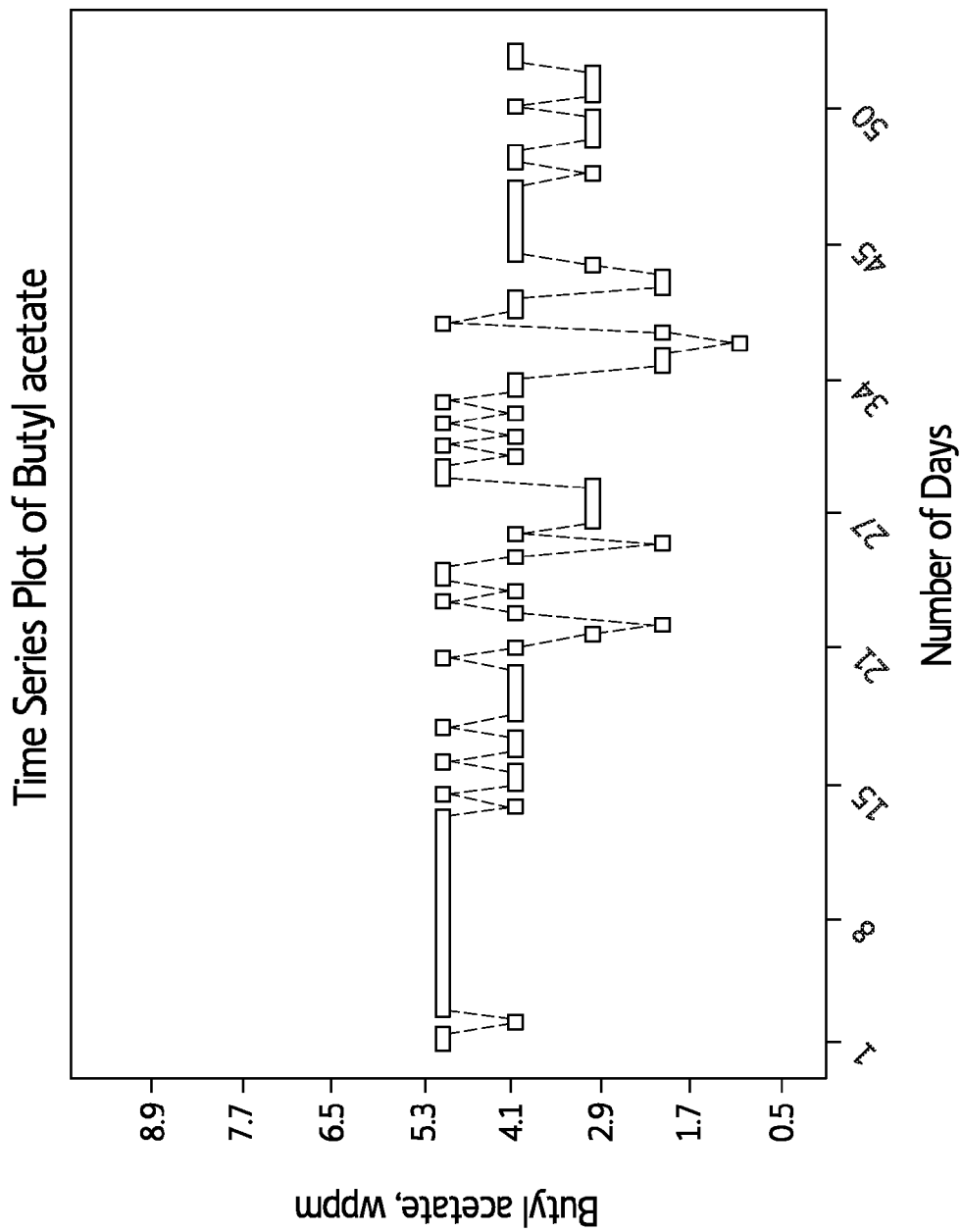
FIG. 4 shows a another time series plot of butyl acetate in a final acetic acid product in accordance with the present invention.

An acetic acid product was prepared as in Example 1, except that the hydrogen partial pressure was 0.30 atm. The concentration of butyl acetate in the acetic acid product was measured over time. The results are shown in FIG. 4. Butyl acetate concentration was consistently below 6 wppm in the acetic acid product.

Example 3

Figure 5:
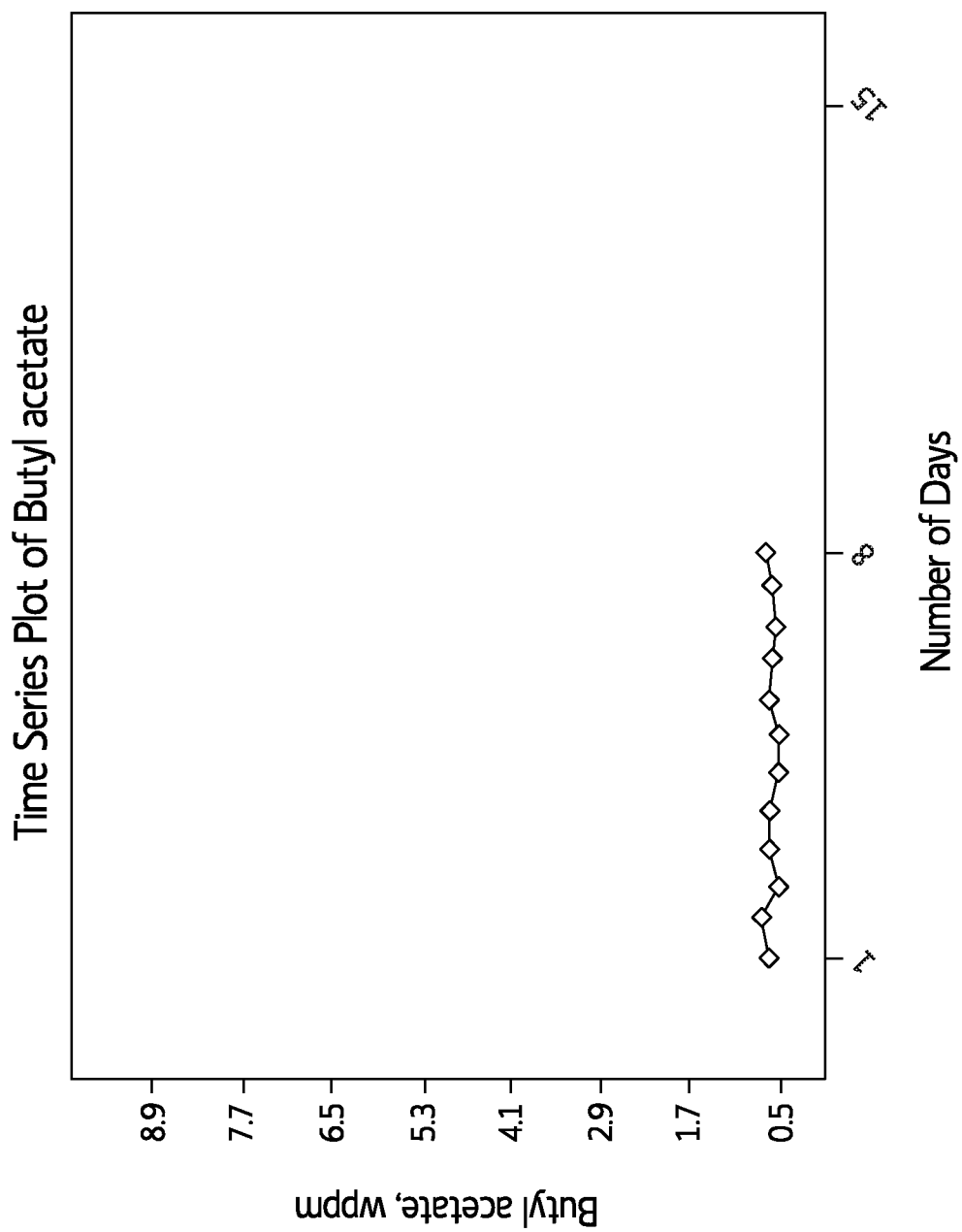
FIG. 5 shows yet another time series plot of butyl acetate in a final acetic acid product in accordance with the present invention.

An acetic acid product was prepared as in Example 1, except that the hydrogen partial pressure was 0.61 atm. The concentration of butyl acetate in the acetic acid product was measured over time. The results are shown in FIG. 5. Butyl acetate concentration was consistently below 2 wppm in the final acetic acid product.

Example 4

An acetic acid product was prepared as in Example 1, except that the reaction medium contained approximately 7 wt. % methyl iodide, approximately 2 wt. % methyl acetate, approximately 2 wt. % water, approximately 1500 wppm rhodium and approximately 9 wt. % to 10 wt. % lithium iodide. The reaction temperature was approximately 200° C. The hydrogen partial pressure was 0.44 atm. Butyl acetate concentration was consistently below 10 wppm in the acetic acid product.

Comparative Example A

As shown in Example 3 of U.S. Pat. No. 6,303,813, an acetic acid product was prepared as follows. The reaction medium contained 10.8 wt. % methyl iodide, 2.5 wt. % methyl acetate, 4.1 wt. % water, 657 wppm rhodium and 8.4 wt. % lithium iodide. The reaction temperature was 191.8° C. The hydrogen partial pressure was 0.46 atm. The reaction medium was flashed and then separated in a light ends column, and drying column as described herein. No PRS was used, and thus acetaldehyde was not removed from a stream derived from the reaction medium. The concentration of butyl acetate in the final acetic acid product 13 wppm.

Comparative Example B

As shown in Example 4 of U.S. Pat. No. 6,303,813, an final acetic acid product was prepared as follows. The reaction medium contained 10.8 wt. % methyl iodide, 2.5 wt. % methyl acetate, 4.1 wt. % water, 657 wppm rhodium and 8.4 wt. % lithium iodide. The reaction temperature was 191.8° C. The hydrogen partial pressure was 0.30 atm. The reaction medium was flashed and then separated in a light ends column, and drying column as described herein. No PRS was used, and thus acetaldehyde was not removed from a stream derived from the reaction medium. The concentration of butyl acetate in the final acetic acid product 16 wppm.

We claim:

1. A process for producing an acetic acid product, comprising:
   providing a reaction medium comprising acetic acid, methanol, methyl acetate, acetaldehyde, less than or equal to 4.1 wt. % water, a rhodium catalyst, methyl iodide and lithium acetate;
   removing acetaldehyde from a stream derived from the reaction medium to form the acetic acid product; and
   contacting the acetic acid product with a metal-exchanged ion exchange resin; and
   maintaining a butyl acetate concentration in the acetic acid product of less than or equal to 10 wppm and maintaining an iodide concentration in the acetic acid product of less than or equal to 100 wppb wherein the process for producing the acetic acid product is carried out at a hydrogen pressure and wherein the butyl acetate concentration is further maintained by adjusting at least one of reaction temperature, hydrogen partial pressure, and rhodium catalyst concentration in the reaction medium and, wherein the hydrogen partial pressure is from 0.3 to 2 atm.

2. The process of claim 1, wherein the hydrogen partial pressure is greater than or equal to 0.4 atm.

3. The process of claim 1, wherein the acetic acid product comprises less than or equal to 250 wppm propionic acid.

4. The process of claim 1, wherein the acetic acid product comprises a displaced metal selected from the group consisting of silver, mercury, palladium and rhodium, and the displaced metal in the acetic acid product is in an amount of less than or equal to 500 wppb, wherein the displaced metal is a metal used in the ion exchange resins.

5. The process of claim 1, wherein the acetic acid product comprises a corrosion metal selected from the group consisting of nickel, iron, chromium, and molybdenum, and the corrosion metal in the acetic acid product is in an amount of less than or equal to 1000 wppb.

6. The process of claim 1, wherein the acetic acid product comprises less than or equal to 50 wppb lithium.

7. The process of claim 1, wherein the reaction medium comprises methyl acetate in an amount from 0.5 to 30 wt. %, a rhodium catalyst in an amount from 200 to 3000 wppm, lithium iodide in an amount from 1 to 25 wt. %, and methyl iodide in an amount from 1 to 25 wt. %.

8. The process of claim 1, wherein the removing acetaldehyde comprises:

(a) separating at least a portion of the reaction medium to provide a vapor overhead stream comprising acetic acid and a liquid recycle;
(b) distilling the vapor overhead stream to yield a purified acetic acid product and a first overhead stream comprising methyl iodide, water, acetic acid, methyl acetate, and acetaldehyde;
(c) distilling at least a portion of the first overhead stream to form a second overhead stream and a liquid phase residuum, wherein the second overhead stream is enriched with acetaldehyde with respect to the at least a portion of the first overhead stream; and
(d) extracting the second overhead stream with water to obtain an aqueous acetaldehyde stream comprising acetaldehyde and a raffinate comprising methyl iodide.

9. The process of claim 8, further comprising condensing and biphasically separating the first overhead stream to form a light liquid phase and a heavy liquid phase, wherein the at least a portion of the first overhead stream distilled in step (c) comprises the light liquid phase.

10. The process of claim 8, further comprising condensing and biphasically separating the first overhead stream to form a light liquid phase and a heavy liquid phase, wherein the at least a portion of the first overhead stream distilled in step (c) comprises the heavy liquid phase.

11. A process for producing an acetic acid product, comprising:
reacting methanol with carbon monoxide in a reactor having a hydrogen partial pressure from 0.3 to 2 atm to yield a reaction medium comprising acetic acid, methanol, methyl acetate, less than or equal to 4.1 wt. % water, acetaldehyde, a rhodium catalyst, methyl iodide and lithium acetate;
removing acetaldehyde from a stream derived from the reaction medium to form the acetic acid product; and
contacting the acetic acid product with a metal-exchanged ion exchange resin; and
maintaining a butyl acetate concentration in the acetic acid product of less than or equal to 10 wppm and maintaining an iodide concentration in the acetic acid product of less than or equal to 100 wppb.

12. The process of claim 11, wherein the butyl acetate concentration is further maintained by adjusting at least one of reaction temperature, hydrogen partial pressure, and rhodium catalyst concentration in the reaction medium.

13. The process of claim 12, wherein the acetic acid product comprises less than or equal to 250 wppm propionic acid.

14. The process of claim 11, wherein the acetic acid product comprises a displaced metal selected from the group consisting of silver, mercury, palladium and rhodium, and the displaced metal in the acetic acid product is in an amount of less than or equal to 500 wppb, wherein the displaced metal is a metal used in the ion exchange resins.

15. The process of claim 11, wherein the reaction medium comprises methyl acetate in an amount from 0.5 to 30 wt. %, a rhodium catalyst in an amount from 200 to 3000 wppm, lithium iodide in an amount from 1 to 25 wt. %, and methyl iodide in an amount from 1 to 25 wt. %.

16. A process for producing an acetic acid product, comprising:
providing a reaction medium comprising acetic acid, methanol, methyl acetate, less than or equal to 4.1 wt. % water, acetaldehyde, a rhodium catalyst, methyl iodide and lithium acetate;
removing acetaldehyde from a stream derived from the reaction medium to form the acetic acid product, wherein the acetic acid product comprises a corrosion metal selected from the group consisting of nickel, iron, chromium, and molybdenum, and the corrosion metal in the acetic acid product is in an amount of less than or equal to 1000 wppb; and
contacting the acetic acid product with a metal-exchanged ion exchange resin; and
maintaining a butyl acetate concentration in the acetic acid product of less than or equal to 10 wppm and maintaining an iodide concentration in the acetic acid product of less than or equal to 100 wppb wherein the reaction is carried out at a hydrogen partial pressure from 0.3 to 2 atm.

17. The process of claim 16, wherein the butyl acetate concentration is further maintained by adjusting at least one of reaction temperature, hydrogen partial pressure, and rhodium catalyst concentration in the reaction medium.

* * * * *